United States Patent [19]

Meade et al.

[11] Patent Number: 5,746,759
[45] Date of Patent: May 5, 1998

[54] REUSABLE ENDOSCOPIC SURGICAL INSTRUMENT

[75] Inventors: John C. Meade, Walpole; John C. Baccus, Wayland, both of Mass.

[73] Assignee: MicroSurge, Inc., Needham, Mass.

[21] Appl. No.: 707,951

[22] Filed: Sep. 10, 1996

Related U.S. Application Data

[60] Continuation of Ser. No. 475,674, Jun. 7, 1995, abandoned, which is a division of Ser. No. 396,890, Mar. 1, 1995, Pat. No. 5,499,992, which is a continuation of Ser. No. 4,790, Jan. 14, 1993, abandoned, and Ser. No. 287,069, Aug. 8, 1994, Pat. No. 5,478,351, which is a continuation of Ser. No. 903,162, Jun. 24, 1992, abandoned.

[51] Int. Cl.$^6$ .................................................. A61B 17/00
[52] U.S. Cl. ........................ 606/170; 606/174; 606/205; 606/207; 128/751
[58] Field of Search .................................. 606/1, 51, 52, 606/83, 170, 171, 174, 205–210; 30/418; 128/750–755

[56] References Cited

U.S. PATENT DOCUMENTS

| | | |
|---|---|---|
| 514,273 | 2/1894 | Priest . |
| 1,275,107 | 8/1918 | Vass . |
| 2,034,785 | 3/1936 | Wappler . |
| 2,113,246 | 4/1938 | Wappler . |
| 2,518,994 | 8/1950 | Miller . |
| 4,569,131 | 2/1986 | Falk et al. . |
| 4,646,751 | 3/1987 | Maslanka . |
| 4,881,550 | 11/1989 | Kothe . |
| 4,962,770 | 10/1990 | Agee et al. . |
| 5,009,661 | 4/1991 | Michelson . |
| 5,052,402 | 10/1991 | Bencini et al. . |
| 5,133,736 | 7/1992 | Bales, Jr. et al. . |
| 5,152,780 | 10/1992 | Honkanen et al. ............ 606/205 |
| 5,174,300 | 12/1992 | Bales et al. . |
| 5,258,006 | 11/1993 | Rydell et al. . |
| 5,290,308 | 3/1994 | Knight et al. ............ 606/205 |
| 5,290,309 | 3/1994 | Kothe ............ 606/207 |

FOREIGN PATENT DOCUMENTS

| | | |
|---|---|---|
| 0165472 | 12/1985 | European Pat. Off. . |
| 0 308 258 | 9/1988 | European Pat. Off. . |
| 0380874 | 8/1990 | European Pat. Off. . |
| 3303335 | 5/1992 | Germany . |
| WO 91/02493 | 3/1991 | WIPO . |

OTHER PUBLICATIONS

Advertisement for "Endo Shears," United States Surgical Corp., (1990).

*Primary Examiner*—William Lewis
*Attorney, Agent, or Firm*—Hamilton, Brook, Smith & Reynolds, P.C.

[57] ABSTRACT

A reusable endoscopic surgical instrument includes a tool assembly and a detachable handle. The tool assembly consists of an outer sleeve to which a surgical jaw assembly such as scissors or graspers is mounted. An inner extension is mounted inside the sleeve and is longitudinally translatable with respect to the sleeve. When the distal end of the extension is in engagement with the jaws of the jaw assembly, translation of the extension causes the jaws to open and close. The extension can be translated out of engagement with the jaws to permit disassembly of the instrument for cleaning and changing jaw assemblies. The tool assembly is retained within the handle assembly. The sleeve is retained within the handle in a longitudinally stationary position with respect to the handle, while the extension is permitted to move longitudinally within the sleeve. Relative rotation between a thumb loop and finger loop on the handle assembly longitudinally translates the extension within the sleeve, and thus opens and closes the jaws. The handle assembly can have a rotatable port which allows the user to select between two instrument configurations. The orientation of the port with respect to the finger loop and thumb loop can be changed without interrupting an operation to allow the user to select a comfortable operating position.

21 Claims, 26 Drawing Sheets

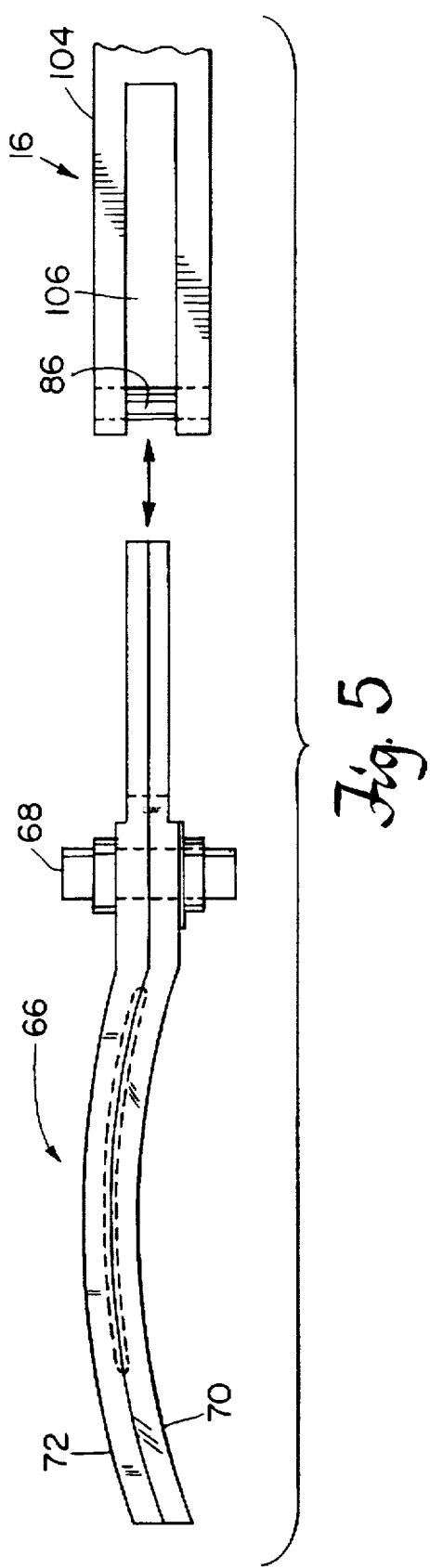
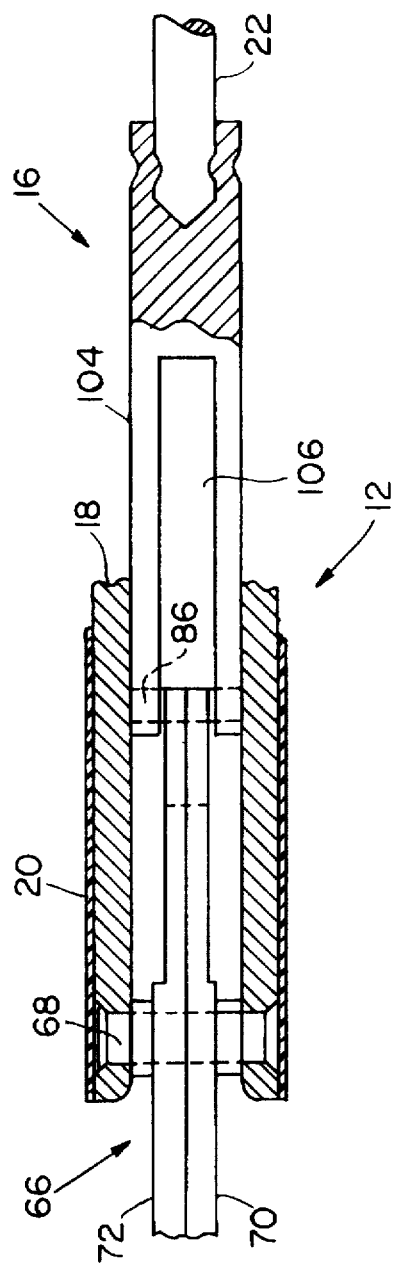
Fig. 5
Fig. 6

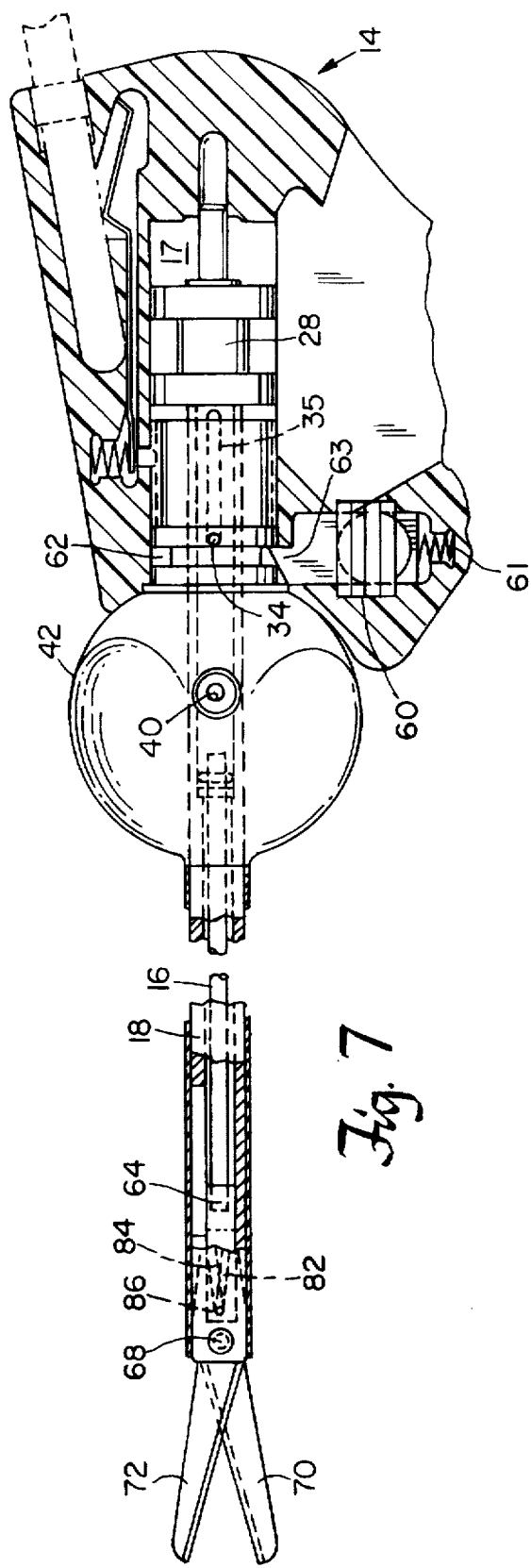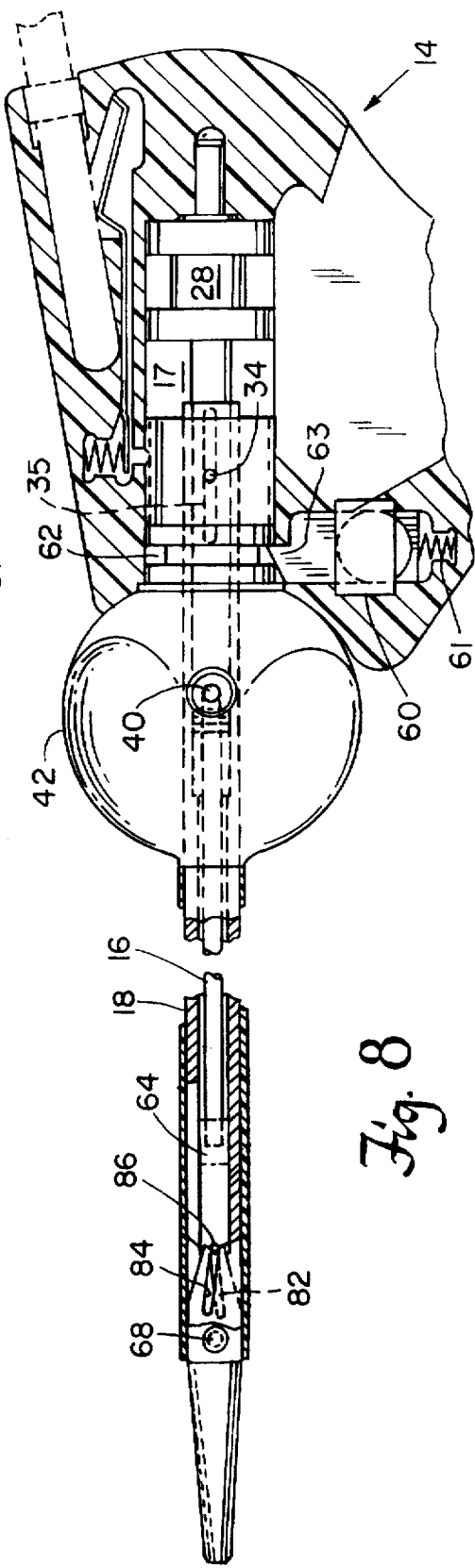

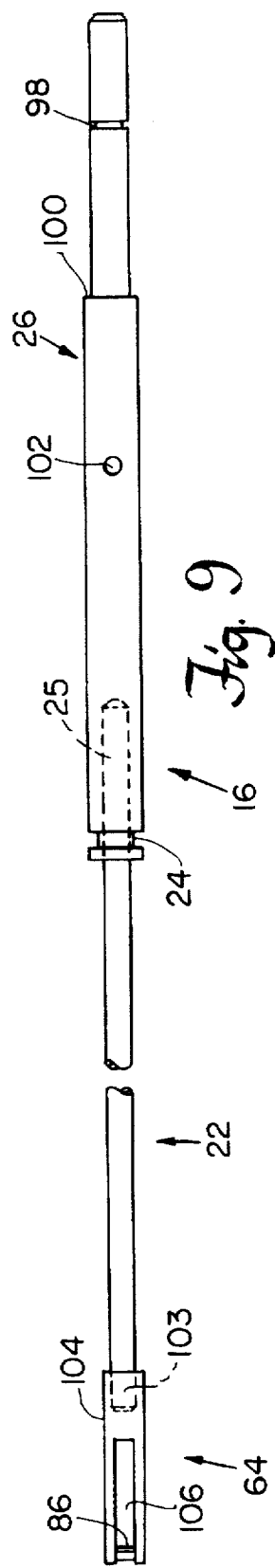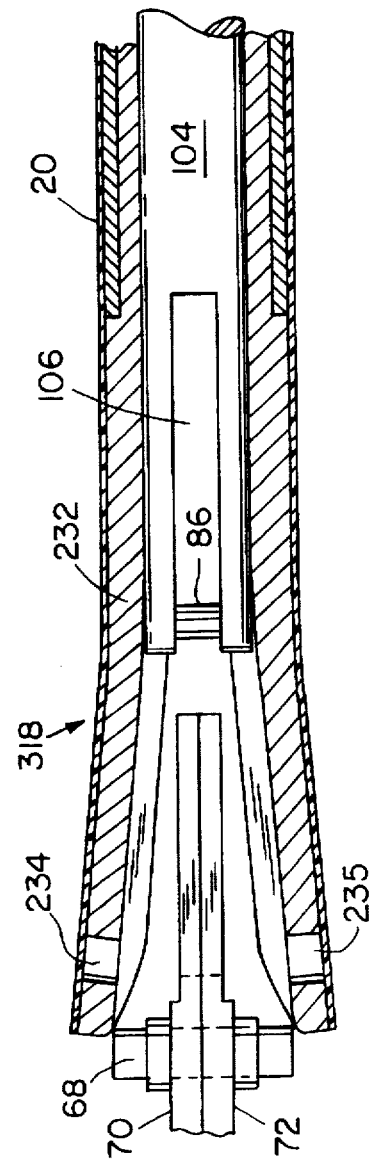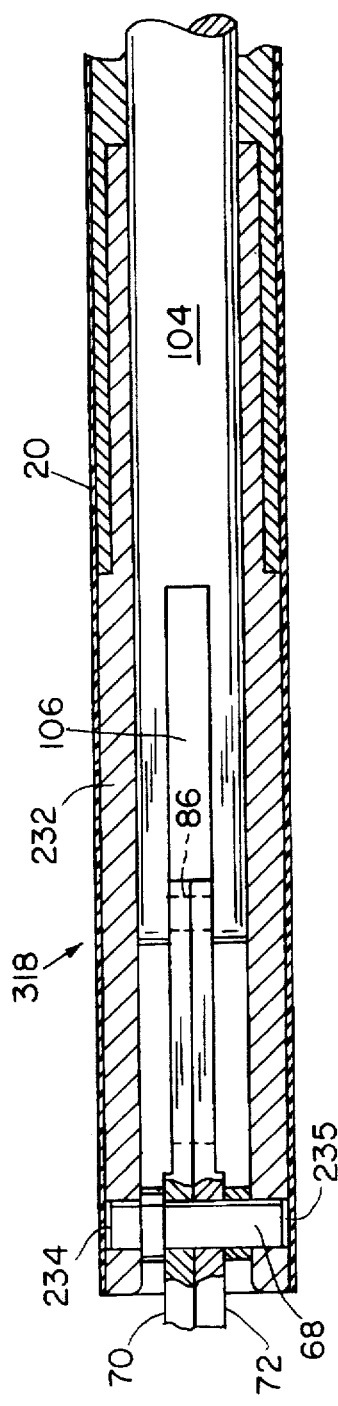

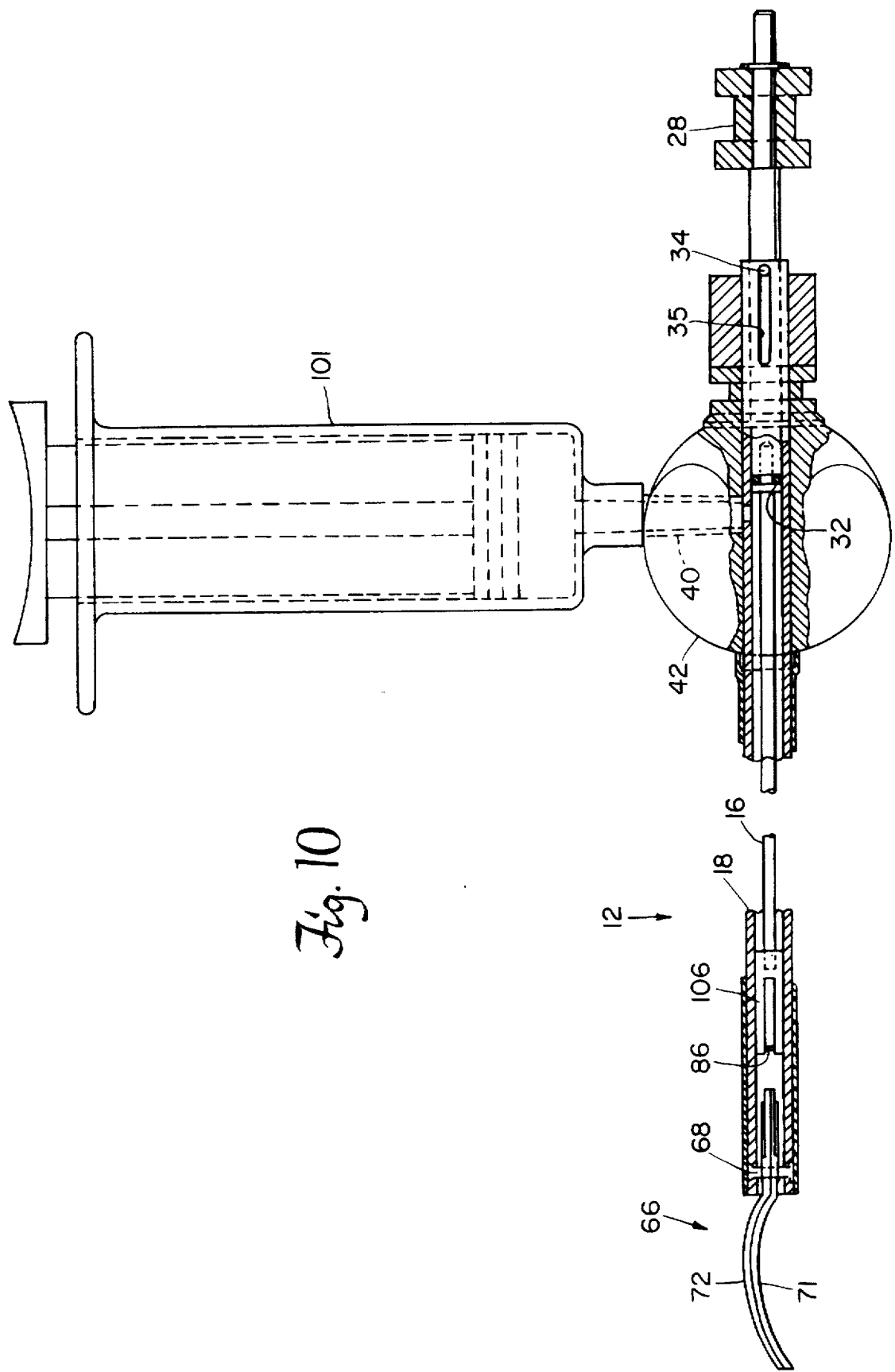

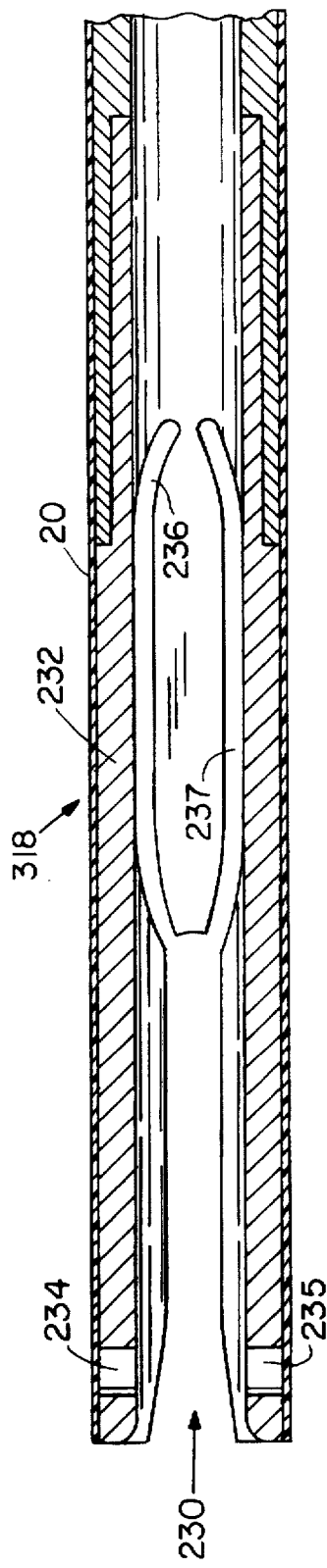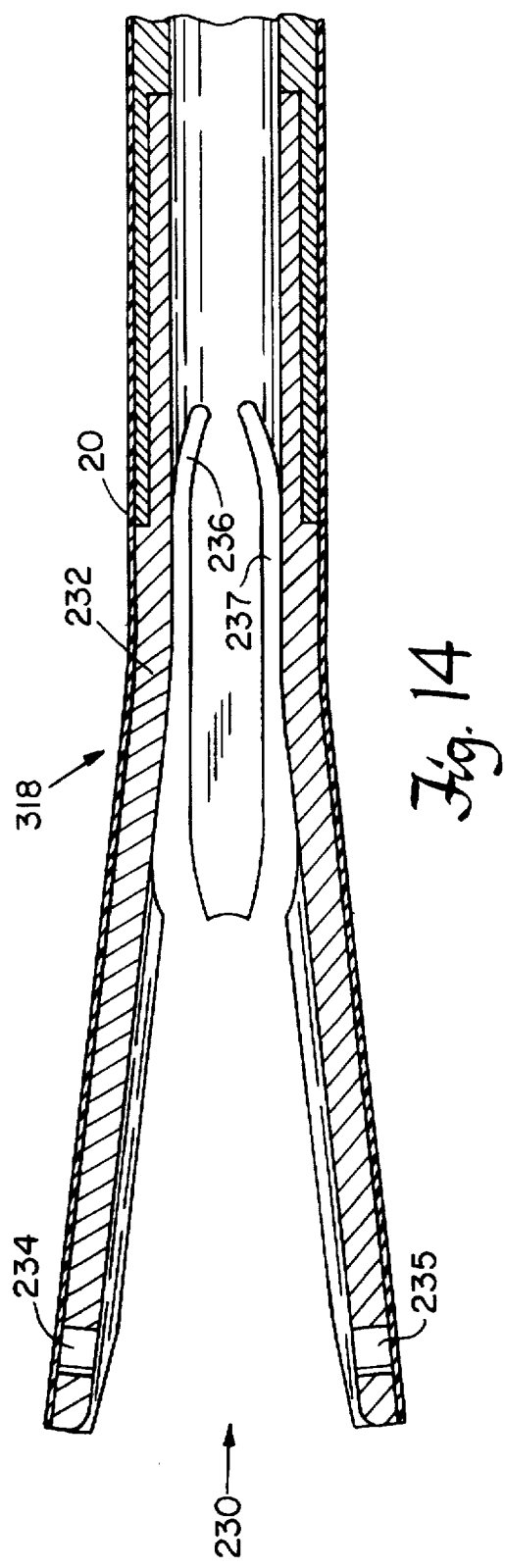
Fig. 13
Fig. 14

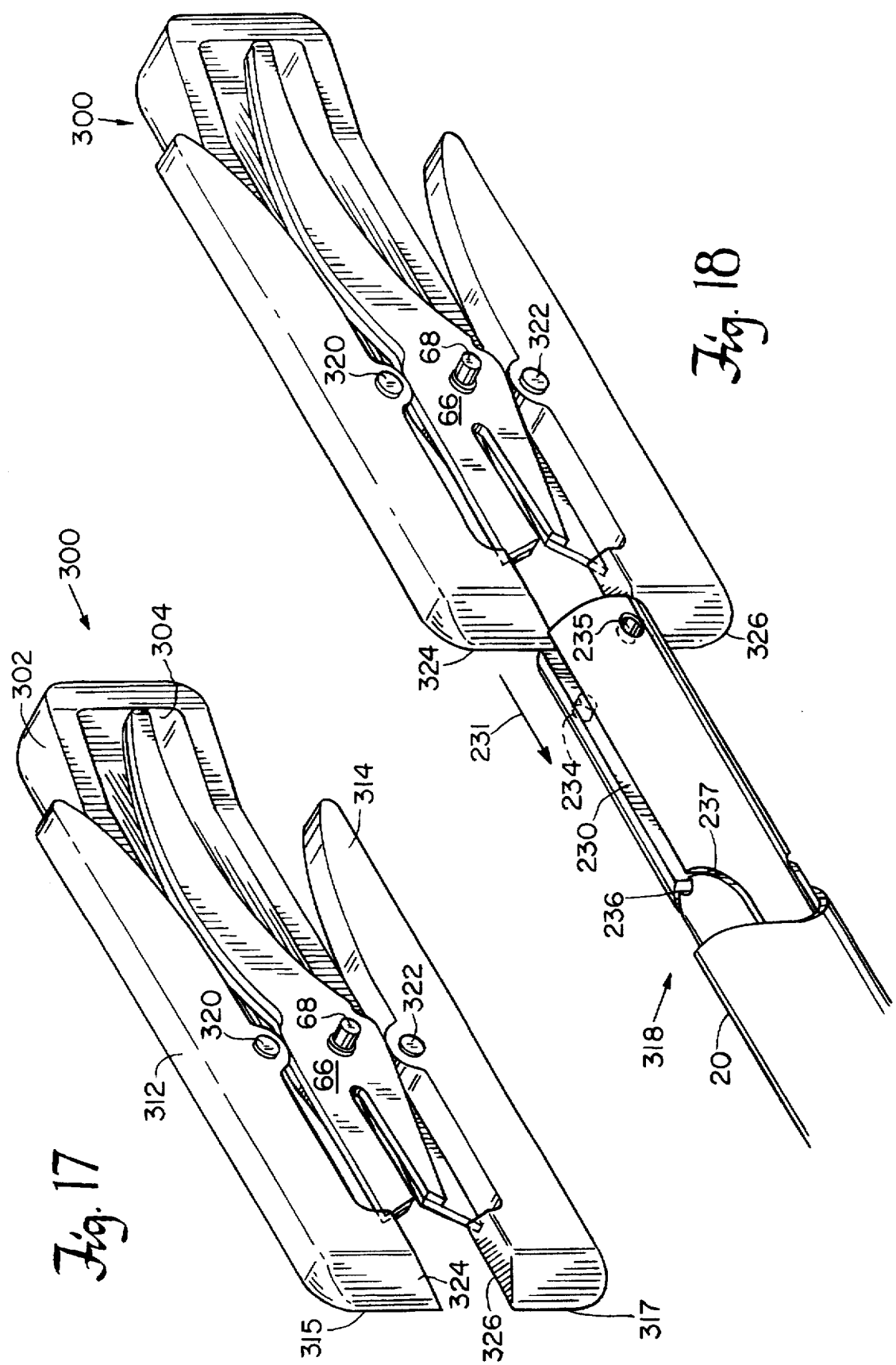

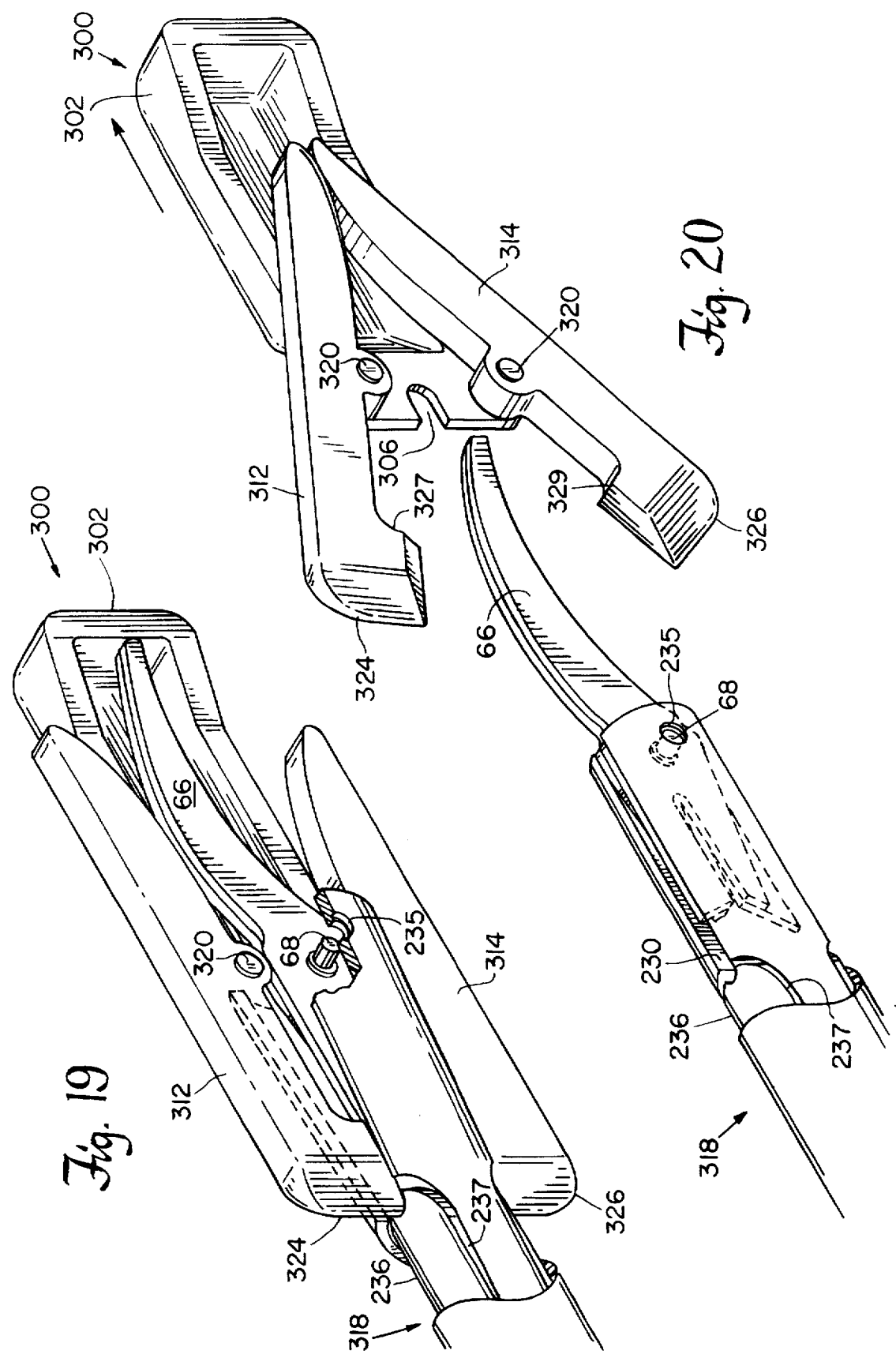

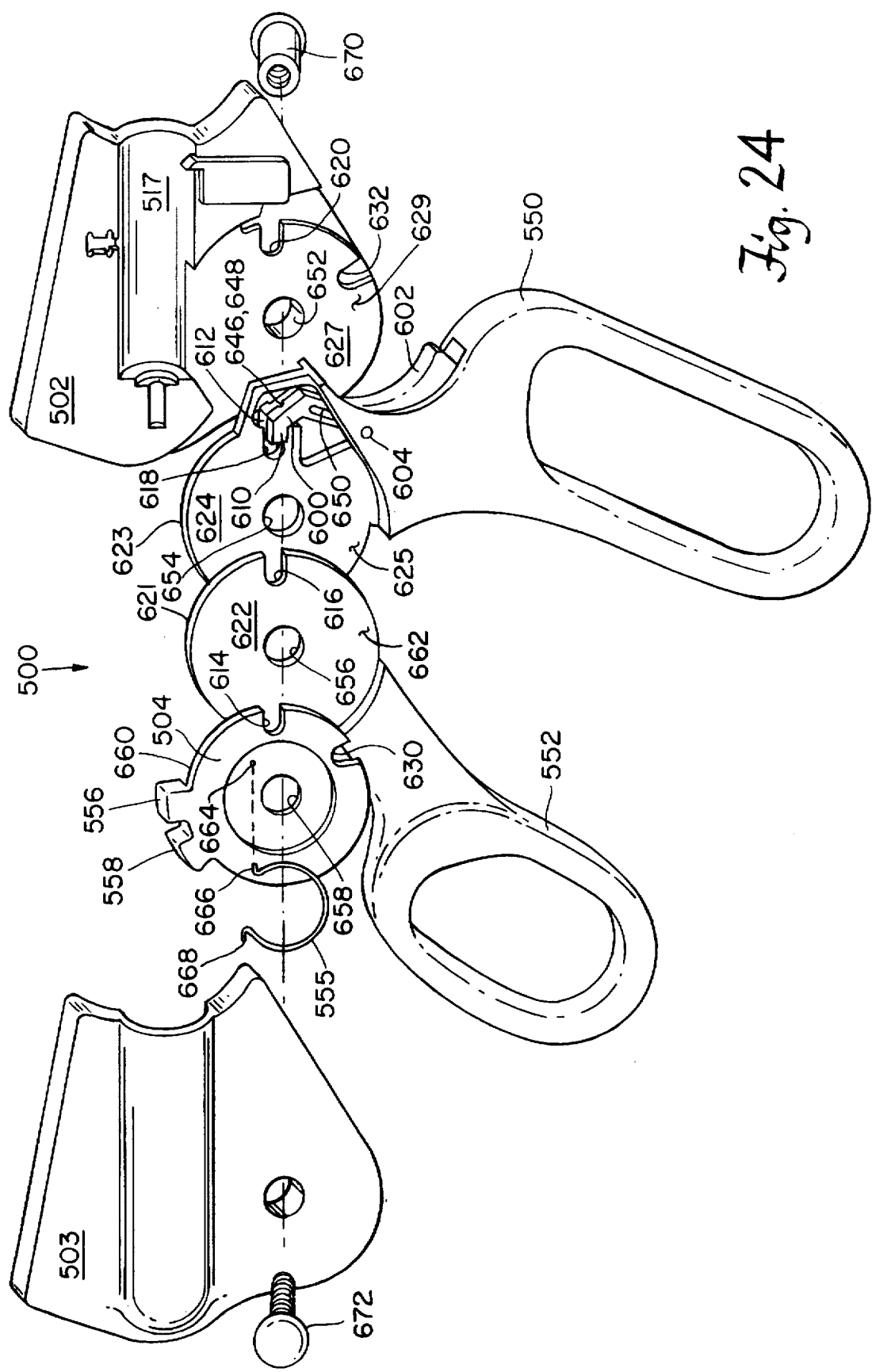

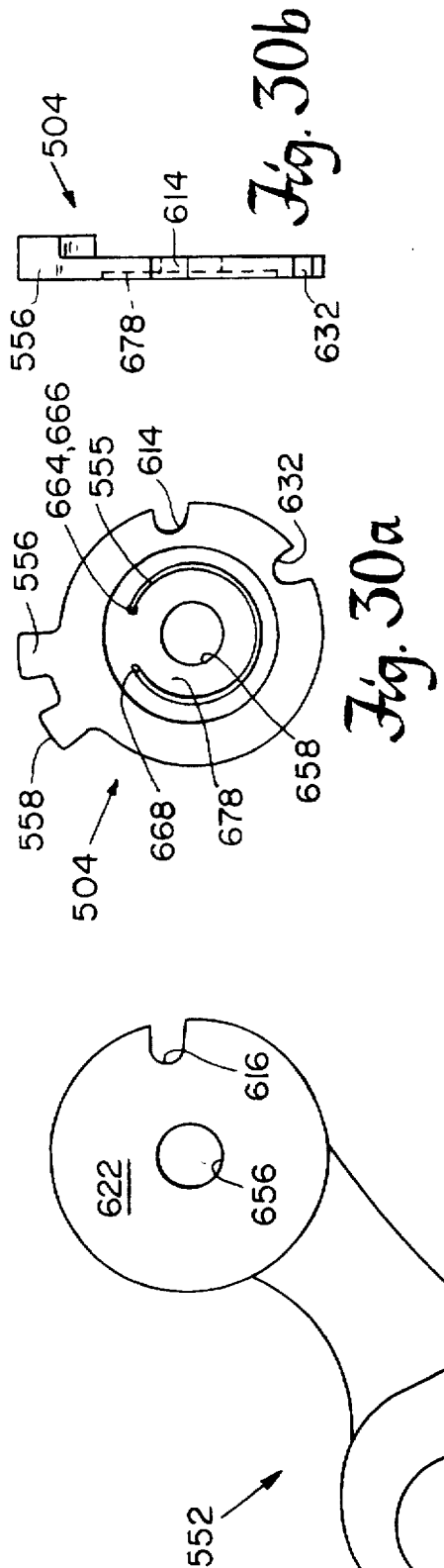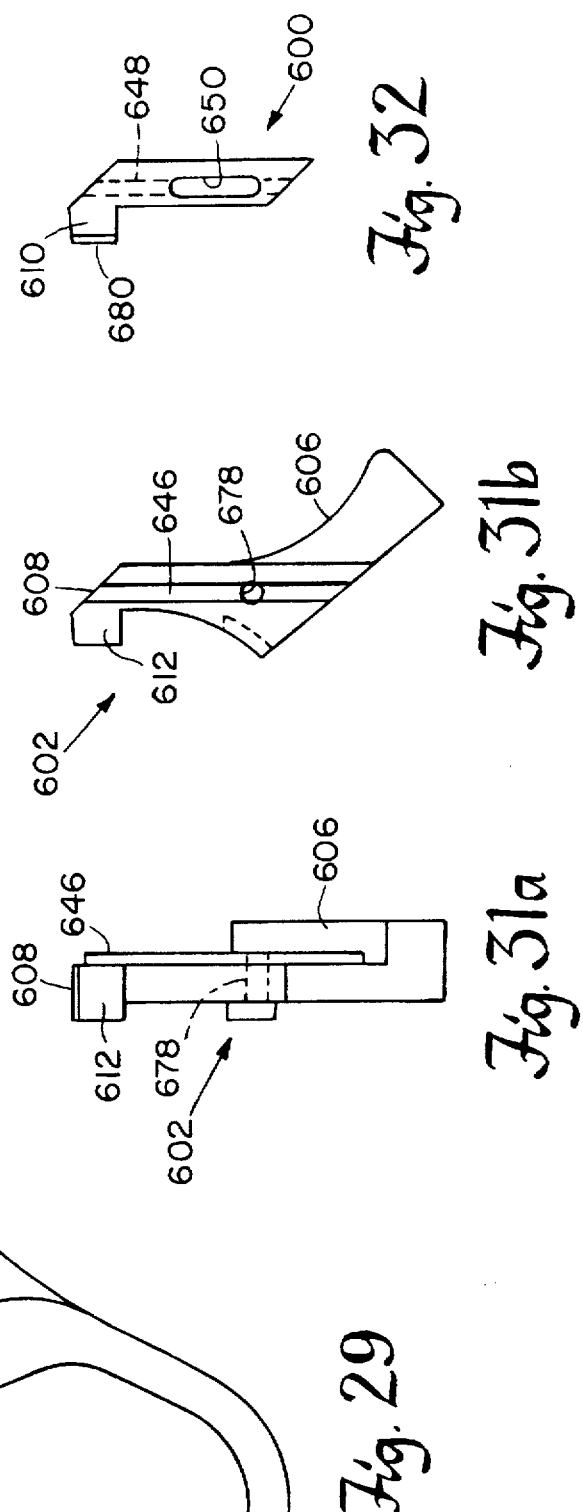

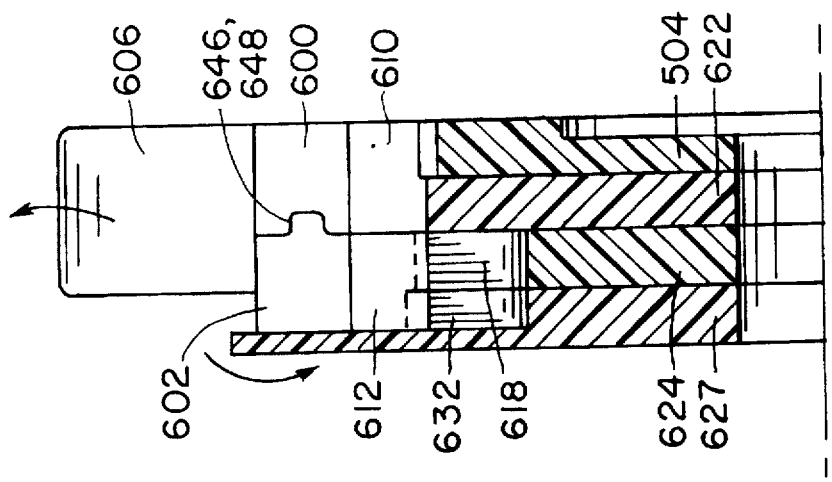
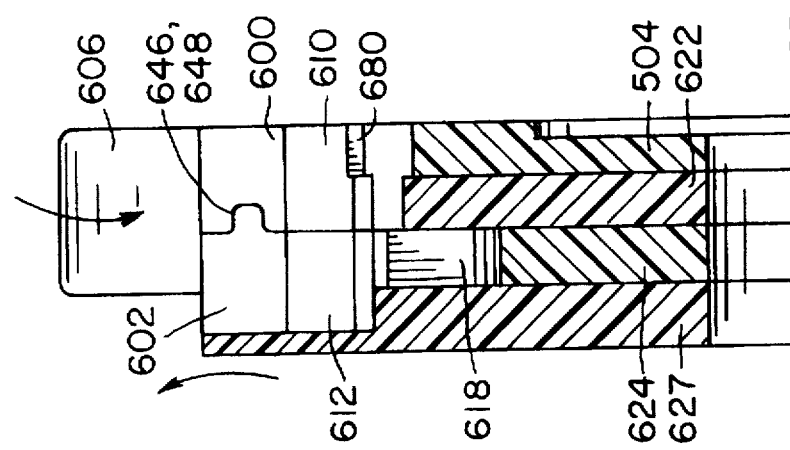
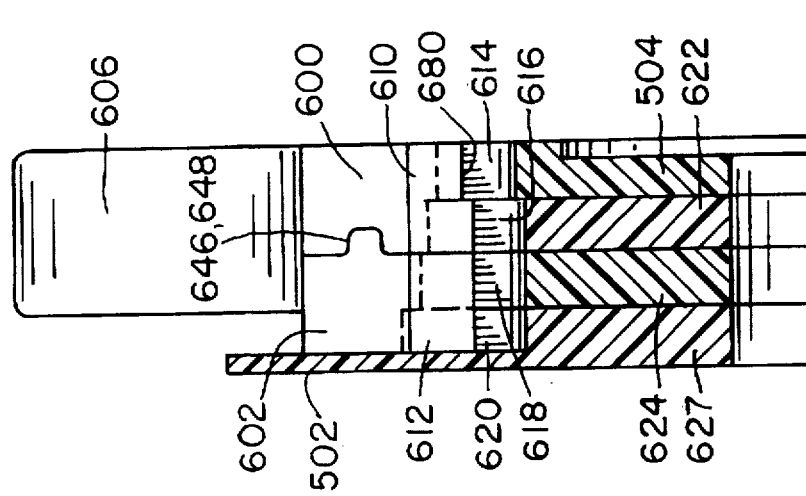

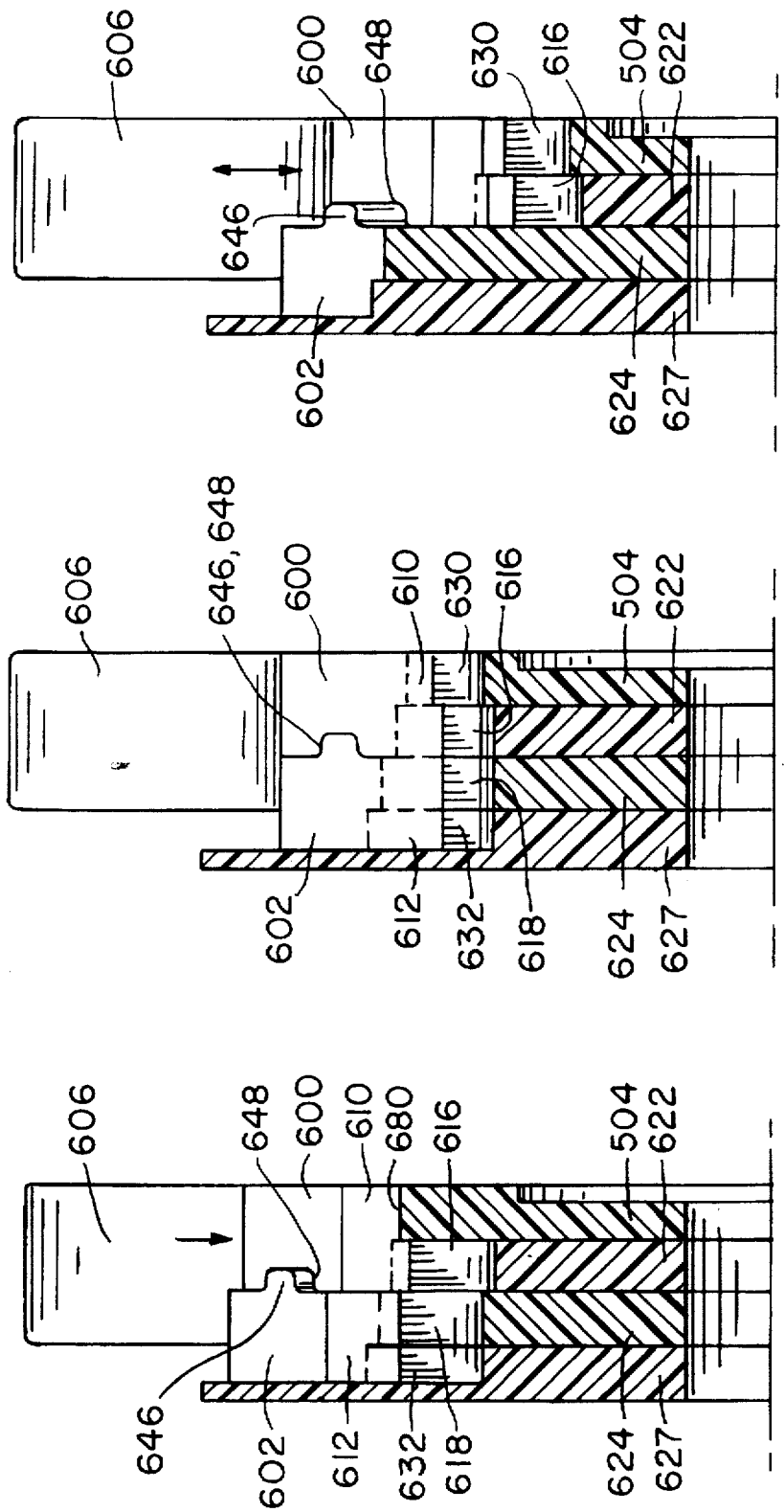

REUSABLE ENDOSCOPIC SURGICAL INSTRUMENT

This application is a continuation of application Ser. No. 08/475,674 filed Jun. 7, 1995, now abandoned, which is a Divisional of U.S. Ser. No. 08/396,890, filed Mar 1, 1995, now U.S. Pat. No. 5,499,992, which is a continuation of U.S. Ser. No. 08/004,790 filed Jan. 14, 1993, now abandoned; and U.S. Ser. No. 08/287,069 filed Aug. 8, 1994, now U.S. Pat. No. 5,478,351, which is a continuation of U.S. Ser. No. 07/903,162 filed Jun. 24, 1992 now abandoned.

BACKGROUND OF THE INVENTION

Since the late 1980s, endoscopic surgery has been growing in popularity at a very high rate. More and more, procedures which have customarily been performed by making large incisions in the patient's body are now being performed by "minimally invasive" or endoscopic methods. It has been estimated that by the year 2000, 40 to 50 percent of all surgeries will be done endoscopically.

Endoscope is the generic term for a viewing tube which can be inserted into the body. In endoscopic surgery, the surgeon makes a hole or portal in the patient's body with a sharp punch-like device called a trocar which is inserted through a sleeve or cannula. The trocar is then removed, leaving the cannula in the portal. The surgeon then inserts desired instruments into the body via the cannula. In many endoscopic procedures, therefore, portals are used to accommodate the instruments needed. These generally include a light source, a TV camera, and surgical tools such as scissors, graspers, dissectors and the like.

With the increase in endoscopic procedures has come an increase in demand for surgical instruments adapted for endoscopic applications. Specifically, the instruments must be small in cross section to minimize trauma of the body. Also, they must be controllable from outside of the body through an extended length. Precise control of instrument operation is imperative as any undesirable movement of the instrument during surgery can have disastrous results.

Also, it is desirable to have reusable instruments to avoid the expense of maintenance. For example, rather than sharpening a dull tool such as a surgical scissors, it can be cost effective to simply replace it. Since only the tool itself needs to be replaced on a regular basis and not the entire instrument which controls it, it may be even more cost effective to provide a tool which can be separated from the instrument and replaced with a new one.

Cleaning of endoscopic instruments can also be a time consuming and expensive procedure. Typically, the instrument must be disassembled to allow cleaning of each of the individual parts. This process is cost effective only in the most expensive surgical instruments. Some low and medium priced surgical instruments which could otherwise be used again must be discarded for want of an efficient cleaning process.

SUMMARY OF THE INVENTION

A reusable endoscopic surgical instrument comprises a tool assembly and a handle assembly. The tool assembly comprises a sleeve to which at least one tool jaw is pivotably mounted. The tool jaws may, for example, be scissor tool jaws or other type of jaw assembly. Each tool jaw has an open-ended slot at its proximal end. An extension is located within the sleeve and is translatable longitudinally within the sleeve. The extension is translatable in and out of engagement with the slots in the proximal ends of the tool jaws. When the extension is in engagement with the tool jaws, longitudinal translation of the extension back and forth causes the jaws to move between open and closed positions. The tool assembly is retained within the handle assembly. The handle assembly actuates the surgical jaw assembly by longitudinally translating the extension back and forth within the sleeve to cause the jaws to open and close.

The jaws are mounted to the distal end of the sleeve via a pivot pin. The pivot pin passes through pivot holes in the jaws and into opposite sides of the sleeve. A drive pin is attached to the distal end of the extension. The drive pin engages the jaws such that longitudinal translation of the extension, when in engagement with the jaws, causes the jaws to open and close.

In one embodiment, the tool assembly consisting of the sleeve, the tool jaws, and the extension are detachable as a unit from the handle. In that embodiment, the entire tool assembly is replaceable. The jaw assembly may be permanently attached to the sleeve. Alternatively, it may be removably attached to the sleeve. To accomplish this, the distal end of the sleeve may be made of an elastic material such that it can spread open to allow the jaw assembly to be inserted or detached with an insertion and detachment device. The jaw assembly can also be made with a spring-loaded compressible pivot which mounts the jaws to the distal end of the sleeve. The pivot is compressed to allow insertion and detachment of the jaw assembly. In these configurations, the jaw assembly is individually replaceable.

In another embodiment, only the sleeve and jaw assembly are detachable from the handle. The extension remains fixed within the handle. Where the jaw assembly is permanently fixed to the sleeve, the sleeve and jaw assembly are replaceable as a unit. Where the jaw assembly is removable from the sleeve, both the sleeve and the jaw assembly are individually replaceable.

The invention also provides for cleaning of the tool assembly between uses. In one embodiment, the tool assembly includes a cleaning port. In that embodiment, cleaning fluid may be introduced from a syringe into the tool assembly via a cleaning port in the tool assembly. The cleaning fluid enters the sleeve to clean the interior of the sleeve as well as the extension and jaw assembly if attached.

Alternatively, where the sleeve is removed from the handle and the extension, cleaning fluid is introduced into the sleeve via the opening of the proximal end of the sleeve. The cleaning fluid runs down the inside of the sleeve and out to the jaw assembly if attached to the sleeve.

Also, the surgical instrument provides for rotation of the surgical tool assembly about the longitudinal axis of the tool assembly within the handle. This allows the user to position the tool assembly in any desired angular orientation while being used. The sleeve comprises a circumferential groove which allows the handle to retain the sleeve against longitudinal movement regardless of the rotational orientation of the tool assembly.

The extension of the surgical instrument can also be sealed to the inside of the sleeve. In one embodiment, an O-ring is mounted in a groove on the extension. The O-ring contacts the inside surface of the sleeve. This seal prevents body fluids and gases from migrating toward the proximal end of the tool assembly during use. It also serves to direct cleaning fluid toward the jaw assembly at the distal end of the tool assembly during the cleaning process.

The surgical instrument can also be used to perform cautery operations. This is facilitated by an electrical connection port provided in the handle assembly.

The handle assembly can also be provided in a dual-port configuration as described in U.S. patent application Ser. No. 07/903,162, now abandoned of which this application is a continuation-in-part. In this configuration, pivoting of the trigger provides translation motion in both of the two ports. The tool assembly can be inserted into either of the ports. When the trigger is pivoted with respect to the handle, the jaws are pivoted between open and closed positions.

The handle assembly can also be provided in a rotatable-port configuration. The rotatable-port handle has a single port in which tool assemblies can be retained and actuated. The port is part of the handle base or housing. In this handle embodiment, the housing can be positioned in one of two possible orientations relative to a finger loop and thumb loop of the handle. The orientation can be changed back and forth between a pistol configuration and a scissor configuration without removing the tool assembly from the handle. Thus, the surgeon can select a comfortable position for the operation being performed without a substantial interruption.

The surgical instrument of the present invention provides numerous advantages over other instruments. The cleanability and replaceability of the tool assemblies and jaw assemblies in the present surgical instrument provide the instrument with a versatility not found in prior systems. The ability to disengage the extension from the jaws facilitates the cleaning and replacement features.

Where the entire tool assembly consisting of the sleeve, the extension, and the jaw assembly are removable as a single unit from the handle assembly, this disengagement feature facilitates the cleaning process. To clean the tool assembly, the extension is pulled back toward the proximal end of the tool assembly to a cleaning position. In this position, the extension is disengaged from the jaws. The O-ring on the extension is located proximal to the cleaning port. Cleaning fluid entering via the cleaning port is therefore directed toward the distal end of the tool assembly.

Where only the sleeve and jaw assembly are removable from the handle and extension, the disengagement of the slots in the jaws and the extension allow easy replacement and cleaning of the tool assembly. In both cases, the open ended slots at the proximal ends of the jaws permit the removal of the jaws from the extension. So, the sleeve and jaw assembly can be removed to introduce cleaning fluid into the sleeve, or the dull jaw assembly can be replaced with a fresh sharp one.

Thus, the present invention provides several multiple use applications for the surgical instrument. Where the sleeve, extension, and jaw assembly are detachable as a single unit, the tool assembly may be used three to four times depending upon the sharpness of the jaws. Between uses, the tool assembly is removed and cleaned via the cleaning port. The disengagement of the extension and the jaws allows the tool assembly to be placed in the cleaning configuration.

Where only the sleeve and jaws are removable from the handle and the extension, the disengagement of the extension from the jaws allows the sleeve and scissors to be removed. Once again the jaws can be used three to four times depending upon their sharpness. When the jaws become dull, the sleeve and jaw assembly are replaced as a unit. Between uses, the sleeve and attached jaw assembly are removed from the handle for cleaning.

Where the jaw assembly is detachable from the sleeve, it may be changed for every use. Thus, each operation is performed with fresh sharp jaws. As in the configurations described above, it is the disengagement of the extension from the jaws of the present invention which provides this advantage. In addition, because the jaw assembly can be easily removed and replaced, different jaw assemblies can be used on the same instrument during surgery. For example, the surgeon can readily change from a scissor to a grasper during an operation.

It should be noted that throughout this application, the term "proximal" refers to a direction or a location which is toward the handle end of the surgical instrument. The term "distal" refers to a direction or a location which is toward the extreme end of the assembled surgical instrument which is further from the handle of the instrument. To illustrate, the distal end of a scissor jaw assembly which may be assembled in an endoscopic surgical instrument would consist of the tips of the scissor blades.

BRIEF DESCRIPTION OF THE DRAWINGS

The foregoing and other objects, features, and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles the invention.

FIG. 5 depicts a scissor type jaw assembly and extension in accordance with the present invention with the extension out of engagement with the jaw assembly.

FIG. 6 depicts the distal end of the tool assembly of the embodiment of FIG. 1.

FIG. 7 is a cut-away view depicting the jaw assembly actuation mechanism of the surgical instrument of FIG. 1 with the jaws in the open position.

FIG. 8 is a cut-away view depicting the actuation mechanism of the surgical instrument of FIG. 1 with the jaws in the closed position.

FIG. 9 depicts the extension of the surgical instrument of the present invention.

FIG. 10 shows the tool assembly of the surgical instrument of FIG. 1 in a cleaning configuration.

FIG. 13 is a cross-sectional view of the distal end of a sleeve in accordance with an embodiment of the present invention.

FIG. 14 is a cross-sectional view of the distal end of a sleeve spread open to receive a jaw assembly in accordance with the present invention.

FIG. 15 is a cross-sectional view of the distal end of a sleeve spread open and receiving a jaw assembly in accordance with an embodiment of the present invention.

FIG. 16 is a cross-sectional view of the distal end of a sleeve with a jaw assembly installed in accordance with the present invention.

FIG. 17 is a perspective view of an insertion tool loaded with jaw assembly.

FIG. 18 is a perspective view of the insertion tool and the distal end of a sleeve before the jaw assembly insertion process.

FIG. 19 is a perspective view of the insertion tool and the distal end of a sleeve during the jaw assembly insertion process.

FIG. 20 is a perspective view of the insertion tool and the distal end of a sleeve after the jaw assembly insertion process.

FIG. 24 is a schematic exploded perspective view of the rotatable-port handle assembly.

FIG. 26a is a schematic side elevational view of the rotatable-port handle assembly in the scissor configuration.

FIG. 26b is a cross-sectional view taken at line A—A of FIG. 25a.

FIG. 29 is a schematic elevational view of the thumb loop of the rot table-port handle assembly.

FIG. 30a is a schematic elevational view of the drive cog of the rotatable-port handle assembly.

FIG. 30b is a schematic elevational view of the drive cog of FIG. 30a rotated 90°.

FIG. 31a is a schematic elevational view of the trigger of the rotatable-port handle assembly.

FIG. 31b is a schematic elevational view of the trigger of FIG. 31a rotated 90°.

FIG. 32 is a schematic elevational view of the slide member of the rotatable-port handle assembly.

FIGS. 35a–35f are cross-sectional views corresponding to FIGS. 34a–34f.

DETAILED DESCRIPTION OF THE INVENTION

Figure 1:
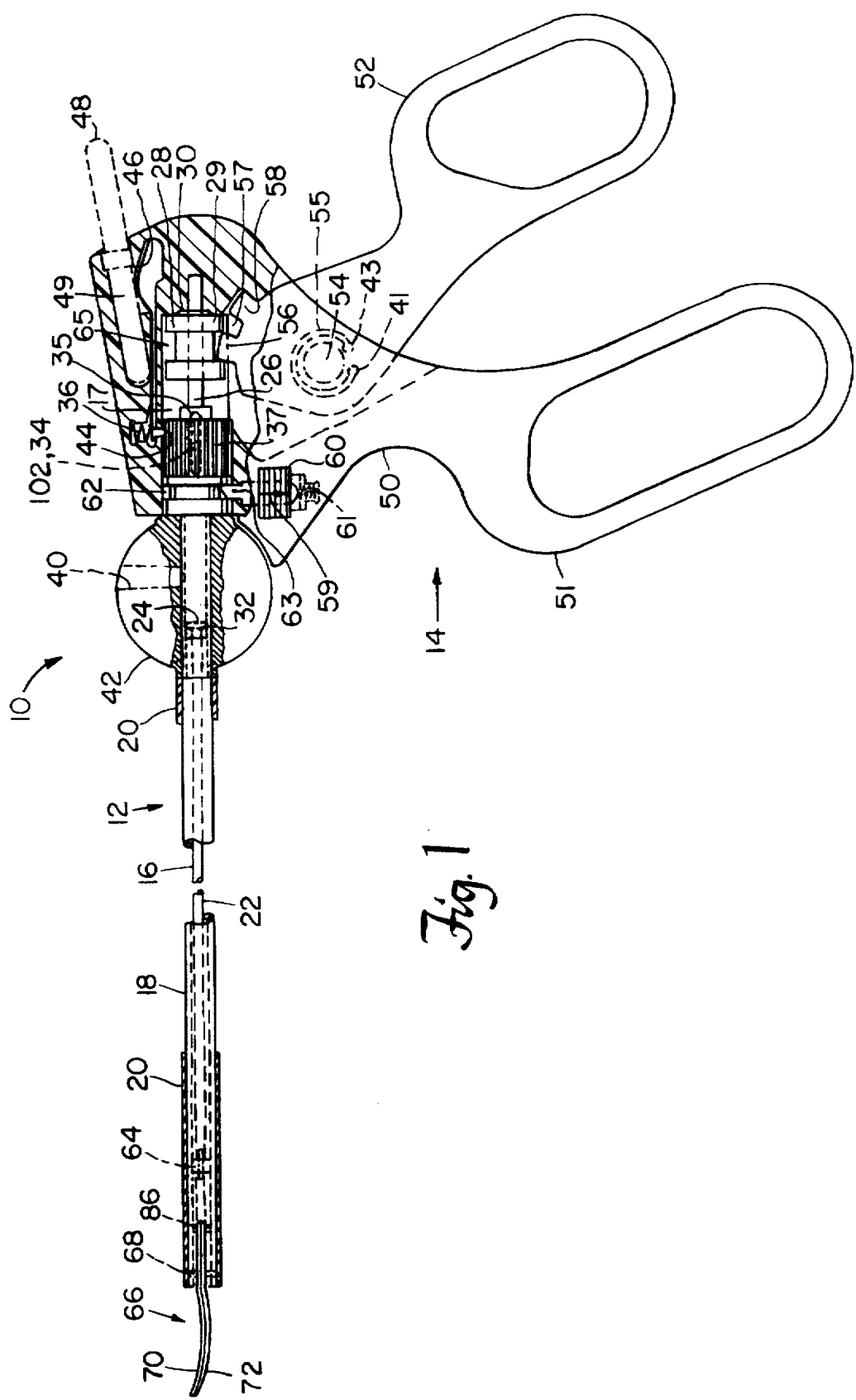
FIG. 1 is a schematic side elevational view of an embodiment of the surgical instrument of the present invention.

FIG. 1 is a side elevational view of an embodiment of the surgical instrument 10 of the present invention. FIG. 1 depicts a tool assembly 12 retained in a handle assembly 14. The tool assembly 12 comprises an inner extension 16 located inside a sleeve 18 and a scissor type jaw assembly 66 attached to the sleeve 18 via a pivot pin 68. A nonconductive cover 20 covers the sleeve 18. The handle 14 comprises a housing or base 50 and a tool actuation trigger or thumb loop 52 pivotably mounted to the base 50 via pivot 54. The base 50 comprises a finger loop 51. During normal use of the instrument, the user places his fingers in the finger loop 51 to steady the base 50 and places his thumb through the thumb loop or actuation trigger 52 to actuate the tool assembly. The handle 14 also comprises a port 17 in which the tool assembly 12 is retained.

The inner extension 16 is longitudinally translatable relative to the sleeve 18. The inner extension 16 comprises three parts: the center span 22, a proximal end 26, and a distal end 64. When the inner extension 16 is translated relative to the sleeve 18, the distal end 64 of the extension 16 engages the jaw assembly 66. As described in detail below, when the extension 16 is translated back toward the proximal end of the tool assembly 12, the distal end of the extension 16 engages the proximal ends of the jaws 70 and 72 to cause them to close. When the extension 16 is translated toward the distal end of the tool assembly 12, the distal end of the extension 16 engages the jaws 70 and 72 to cause them to open.

The extension 16 is sealed to the inside surface of the sleeve 18 by O-ring 32. The O-ring 32 is mounted in a slot 24 in the extension 16. When the extension 16 is located within the sleeve 18, the O-ring contacts the inside surface of the sleeve 18, thus sealing the extension 16 to the sleeve 18. This seal prevents body fluids and gases such as carbon dioxide from traveling to the proximal end of the tool assembly 12 during surgery. It also prevents cleaning fluids from traveling to the proximal end of the tool assembly 12 during a cleaning process to be described below in detail.

The tool assembly 12 can be rotated about its longitudinal axis as a single unit within the handle 14. Rotating knob 42 is attached to the sleeve 18. The extension 16 and sleeve 18 are coupled to each other via a pin 34 in the extension 16 and a slot 35 in the sleeve 18. The pin 34 is pressed into a hole 102 in the extension 16 and protrudes from the extension 16. A slot 35 is cut in the wall of the sleeve 18. The extension 16 and sleeve 18 are assembled such that the end of pin 34 protrudes into the slot 35.

To rotate the tool assembly 12, the user rotates the rotating knob 42. This imparts rotational motion to the sleeve 18. Because the extension 16 and sleeve 18 are coupled by the pin 34 and slot 35 as described above, the extension 16 also rotates. When the sleeve 18 and extension 16 are rotated, the jaw assembly 66 is carried in the rotation by pivot pin 68.

The rotation of the tool assembly 12 is controlled such that the tool assembly 12 is rotated within certain indexed increments. This is accomplished by the index rotator 37, the spring 36, and the detent 44. The index rotator 37 is fixedly attached to the sleeve 18. The detent 44 is biased by spring 36 to engage the teeth on the outer surface of the index rotator 37. As the tool assembly 12 and the index rotator 37 are rotated, the detent 44 moves in and out of meshing engagement with the grooves on the index rotator 37. When a desired rotational angle is selected, the spring 36 provides sufficient force to the detent 44 to maintain the index rotator 37 and the tool assembly 12 stationary against inadvertent rotation.

The tool assembly 12 is retained within the port 17 of the handle 14 by engagement of the tapered end 63 of the spring-loaded retaining knob 60 with the retention groove 62 on the rotating knob 42. The retaining knob 60 is spring biased by spring 61 toward the engagement position. When the tool assembly 12 is inserted into the port 17, the end 63 of retaining knob 60 engages the retention groove 62 to retain the tool assembly 12 in place.

As described previously, actuation of the jaw assembly 66 is controlled by the longitudinal translation of the extension 16 within the sleeve 18. This longitudinal translation is controlled by the actuation trigger 52 of the handle 14. A spool 28 is fixedly attached to the proximal end 26 of the extension 16. The spool 28 is retained on the proximal end 26 of the extension 16 by retaining clip 30.

When the tool assembly 12 is installed in the port 17 of the handle 14, tab 56 on actuation trigger 52 meshes with translation groove 65 in the spool 28. As the actuation trigger 52 is rotated about pivot 54, the tab 56 moves within the port 17, carrying the spool 28 and the extension 16 with it. Thus, the angular motion of the actuation trigger 52 is translated into linear motion of the spool 28.

When the actuation trigger 52 is rotated in the clockwise direction, the spool 28 and the extension 16 are translated back toward the proximal end of the surgical instrument 10. As will be discussed below in detail, this proximal translation of the extension 16 with respect to the sleeve 18 causes the jaws 70 and 72 to move toward the closed position.

When the actuation trigger 52 is rotated in the counter-clockwise direction, the extension 16 is translated forward toward the distal end of the surgical instrument 10. This distal translation of the extension 16 causes the jaws 70 and 72 to open.

The actuation trigger 52 is spring biased by return torsion spring 55. The return spring 55 biases rotation of the actuation trigger 52 in the counter-clockwise direction. This bias tends to translate the extension 16 toward the distal end of the tool assembly 12 and thus tends to open the jaws 70 and 72. One end 43 of the return spring 55 is fixedly attached to the actuation trigger 52, and the other end 41 is fixedly attached to the handle base 50. The return spring 55 is radially compressed before attachment to the instrument such that the counter-clockwise rotational bias is attained. In the embodiment of FIG. 1, as shown, the return spring 55 is compressed as far as possible because the actuation trigger 52 is rotated as far as possible in the clockwise direction in opposition to the bias.

The surgical instrument 10 of the present invention also provides for the electrical connections required for cautery procedures. These electrical connections are effected via the electrical connection port 49 in the handle 14.

The electrically conducting spring clip 46 is exposed to the interior of the port 49. The clip 46 runs distally toward the front of the handle to spring 36 and detent 44. The distal end of the spring clip is squeezed between the spring 36 and the detent 44 thus making a connection to the index rotator 37. The spring clip 46, the detent 44, the index rotator 37, the sleeve 18, and the jaw assembly 66 are all electrically conducting. Therefore, an electrical connection is made from the electrical connection port 49 to the jaw assembly 66. When desired, an electrical connection can be made via an electrical connector 48 inserted into electrical connection port 49.

The non-conductive cover 20 on the outside of the sleeve 18 serves to insulate the electrified sleeve 18 from tissue in the body. This allows the user to limit the cautery operation to a well defined area of tissue.

The tool assembly 12 and the handle 14 are detachable. To remove a tool assembly 12 from the handle 14, the user slides the spring-loaded retaining knob 60 down in the direction shown by arrow 59. This causes the end 63 of the knob 60 to disengage the retention groove 62 in the rotating knob 42. Next, the user may grasp the rotating knob 42 and pull the tool assembly 12 distally out of the port 17. Alternatively, the user may, while holding knob 60 down, rotate the actuation trigger 52 as far as possible in the counter-clockwise direction. This will cause tab 56 to disengage translation groove 65 in spool 28. In addition, tab 58 will engage the back side of spool 28 to urge the extension 16 and the tool assembly 12 out of the port 17. After the spool 28 clears the tabs 56 and 58, the user may simply slide the tool assembly 12 the rest of the way out of the port 17.

Figure 2:
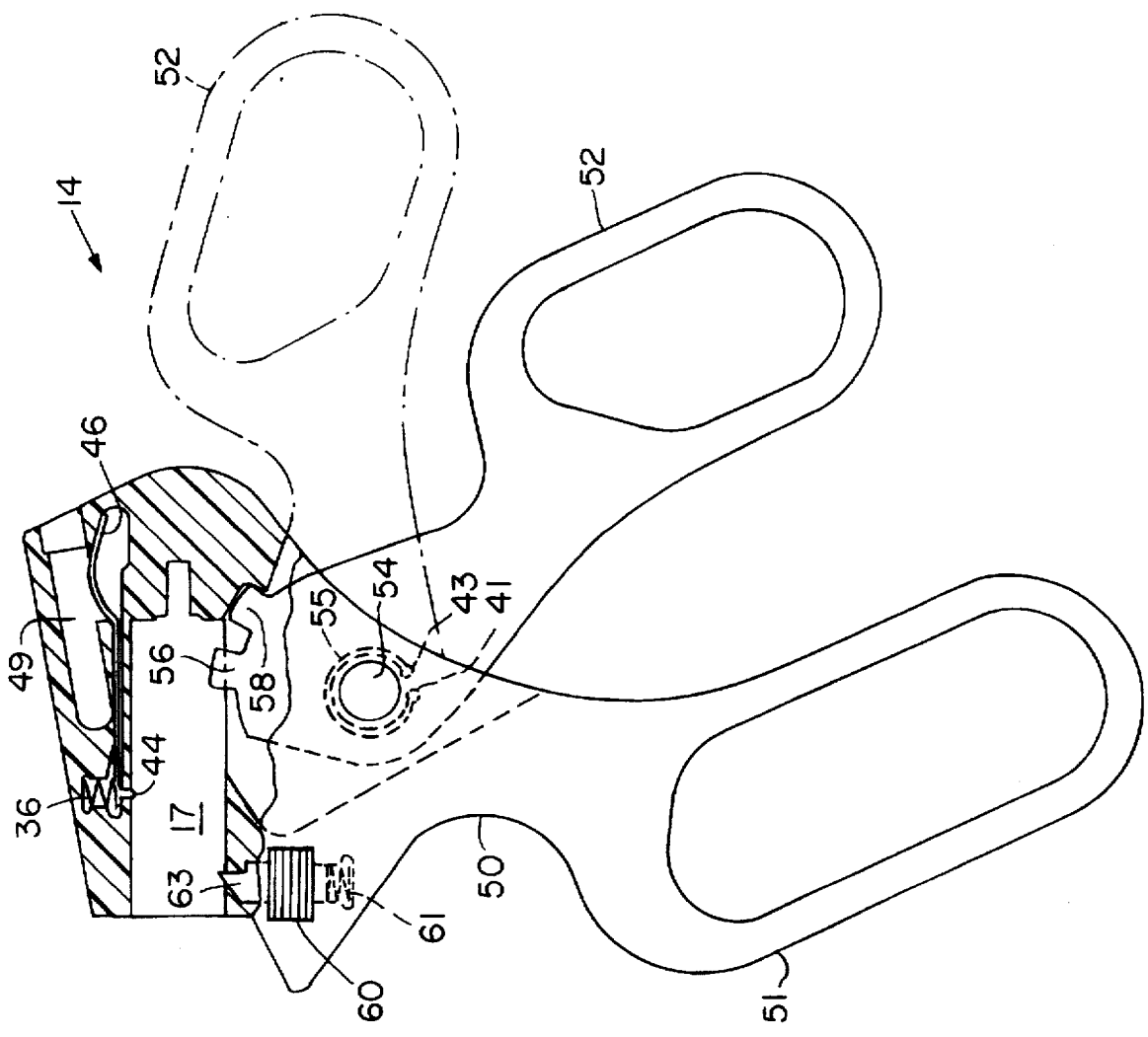
FIG. 2 is a schematic side elevational view of a handle assembly the surgical instrument of FIG. 1.

FIG. 2 shows the handle 14 of the surgical instrument 10 of FIG. 1 with the tool assembly 12 removed. Referring to FIGS. 1 and 2, to install a tool assembly 12 into a handle 14, the user first rotates the actuation trigger 52 as far as possible in the counter-clockwise direction (shown in phantom lines). This causes tab 58 to protrude into the port 17. Next, the user simply slides a tool assembly 12 into the port 17. Because the end 63 of the retaining knob 60 is tapered, the user need not slide the knob 60 out of the way to allow the tool assembly 12 to slide back into the port 17. The knob 60 will simply be moved out of the way by interfering pieces of the tool assembly 12 until the retention groove 62 in the rotating knob 42 is engaged by the end 63 of the knob 60.

During installation of a tool assembly 12, the spool 28 slides back within the port 17. As it does so, the back side of the spool 28 engages the tab 58 protruding into the port 17. The rearward motion of the spool 28 forces the tab 58 out of the way by forcing the actuation trigger 52 to rotate in the clockwise direction. The back ridge portion 29 of the spool 28 then engages with the groove 57 between tabs 56 and 58 on the actuation trigger 52. Finally, as the spool 28 slides all the way back into the port 17, the rotation of the actuation trigger 52 causes the tab 56 to engage the translation groove 65 on the spool 28. When the end 63 of the knob 60 engages with the retention groove 62 on the rotating knob 42, the tool assembly 12 is retained within the handle 14 and is ready for use.

Referring to FIG. 1, the tool assembly 12 is also provided with a cleaning port 40 in the rotating knob 42. This port 40 allows for the introduction of cleaning fluid into the tool assembly 12. The port 40 is a luer taper configuration. A syringe full of cleaning fluid (not shown) having an end with a mating luer taper may be inserted into the port 40. The cleaning fluid is then introduced into the interior of the tool assembly 12 between the extension 16 and the inside surface of the sleeve 18. As will be described below in detail, this cleaning process may be performed when the tool assembly 12 is removed from the handle 14.

In the preferred embodiment, when the tool assembly is installed in the handle 14, the proximal end of the port 17 prevents the spool from moving back proximally far enough for the O-ring seal 32 to travel to the proximal side of the cleaning port 40. Thus, when the tool assembly 12 is installed in the handle 14, the O-ring seal 32, positioned as shown in FIG. 1, prevents body fluids from traveling up the tool assembly 12 to the handle 14.

In this embodiment, the cleaning process is carried out with the tool assembly detached from the handle. With the tool assembly detached, the proximal end of the port 17 does not interfere with the travel of the extension 16. The O-ring seal 32 can be positioned on the proximal side of the cleaning port 40. Cleaning fluid enters the tool assembly 12 via the port 40 and runs to the distal end of the tool assembly 12. In other embodiments, the proximal end of the port 17 does not inhibit travel of the extension 16. In these embodiments, the cleaning process can be performed with the tool assembly attached to the handle.

Figure 3:
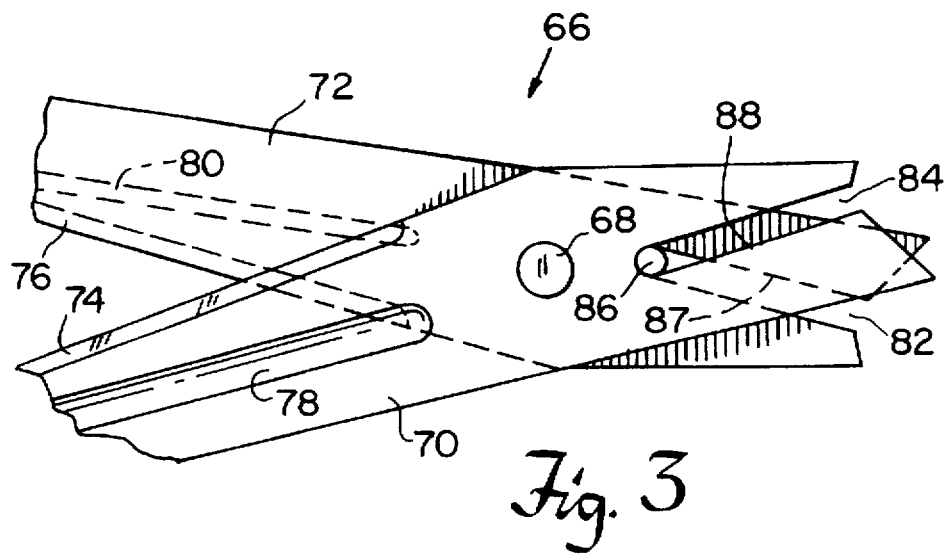
FIG. 3 depicts the blades of a scissor type jaw assembly in accordance with the present invention in an open position.
Figure 4:
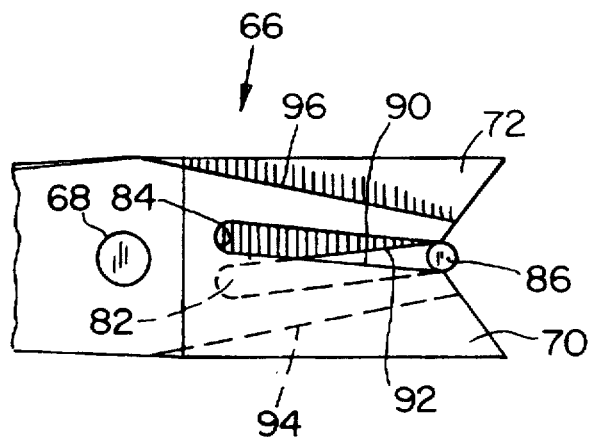
FIG. 4 depicts the blades of a scissor type jaw assembly in accordance with the present invention in a closed position.

FIGS. 3 and 4 depict a scissor type embodiment of the jaw assembly 66 used in the surgical instrument 10 of the present invention shown in open and closed positions, respectively. Referring to FIG. 3, jaws 70 and 72 are shown pivotably mounted to each other via pivot 68. Jaw 70 comprises cutting surface 74, and jaw 72 comprises cutting surface 76. Depressions 78 and 80 in jaws 70 and 72 respectively allow the jaws to mesh properly as they pivot throughout their range of operation. The distal end of each jaw is twisted with respect to the proximal end of each jaw such that the jaws are biased toward each other by opposing angles to provide a proper positive cutting action during operation. In the preferred embodiment, the twist angle of each jaw is approximately 2.5°.

Each jaw also comprises an open ended slot at its proximal end. Jaw 72 comprises open ended slot 82, and jaw 70 comprises open ended slot 84. The open ended slots 82 and 84 are engageable by drive pin 86. It should be noted that drive pin 86 is not part of the jaw assembly 66; it is coupled to the distal end 64 of the inner extension 16 as described below in connection with FIG. 9.

FIG. 3 shows the drive pin 86 positioned as far as possible toward the distal end of the jaw assembly 66. In this configuration, the jaws are in an open position. If the drive pin 86 is moved toward the proximal ends of the slots 82 and 84, the jaws 70 and 72 will tend to move toward a closed position. As the drive pin 86 is moved proximally, it engages the inner wall 87 of slot 82 and the inner wall 88 of slot 84. This causes the inner walls of the slots to spread apart from each other and further causes the jaws 70 and 72 to close.

FIG. 4 depicts the jaws 70 and 72 in the closed position. Drive pin 86 has been moved out to the proximal ends of slots 82 and 84. It should be noted that further proximal translation of the drive pin 86 will cause the drive pin 86 to disengage the slots 82 and 84, but such translation is normally prevented by the handle assembly. The proximal ends of the jaws 70 and 72 are formed at angles which ensure proper engagement of the drive pin 86. When the drive pin 86 is disengaged from the slots in the jaws, distal translation of the drive pin 86 will cause it to engage the slots regardless of the pivotal orientation of the blades with respect to each other, even though the slots are not aligned. This effect is due to the angles at which the proximal ends of the jaws are formed.

To open the blades, the drive pin 86 can be translated within the slots 82 and 84 toward the distal end of the jaws 70 and 72. As the drive pin 86 moves along the slots, it engages inner wall 92 of slot 82 and inner wall 90 of slot 84 to drive the blades apart. The angled side surfaces 94 and 96 on jaws 72 and 70 respectively are provided to prevent the jaws from interfering with the sleeve 18 when the jaws are in an open position. They also serve as a stop to prevent the jaws 70 and 72 from pivoting too far when the drive pin 86 is disengaged from the slots.

FIG. 5 depicts a jaw assembly 66 and the distal end of the extension 16 of the present invention. The distal end of the extension 16 comprises a clevis 104 which carries the drive pin 86. The drive pin 86 spans a gap 106 in the clevis 104. The clevis 104 and drive pin 86 are shown out of engagement with the proximal ends of the jaws 70 and 72.

FIG. 6 depicts the distal end of the tool assembly 12. The jaw assembly 66 is shown attached to the sleeve 18 by the pivot pin 68. The distal end of the extension 16 is shown within the sleeve 18. The extension 16 comprises the distal end of the center span 22 attached to the clevis 104. The details of the extension 16 will be described below in detail. In FIG. 5, the drive pin 86 carried by the clevis 104 is shown engaging the proximal ends of the jaws 70 and 72.

FIGS. 7 and 8 depict the relationship between the position of the spool 28 within the port 17 of the handle 14 and the position of the jaws 70 and 72. FIG. 7 depicts the configuration in which the jaws are open, and FIG. 8 depicts the configuration in which the jaws are closed.

Referring first to FIG. 7, the tool assembly 12 is shown retained in the port 17 of the handle 14. The end 63 of the spring-loaded retention knob 60 is shown in engagement with the retention groove 62 on the rotating knob 42. In the figure, spool 28 is shown translated toward the distal end of the port 17. Consequently, extension 16 is translated toward the distal end of the tool assembly 12. Pin 34 in the extension 16 is shown at the distal end of slot 35 in the sleeve 18. Thus, drive pin 86 is located at the distal ends of slots 82 and 84 of the jaws 70 and 72. As a result, the jaws are in the open position.

Referring now to FIG. 8, the closed-jaws configuration is depicted. Spool 28 has been translated to the proximal end of the port 17. The extension 16 has been pulled back in the proximal direction. Pin 34 in the extension 16 is located half way between the distal end and the proximal end of the slot 35 in the sleeve 18. In contrast, in the open-jaws configuration shown in FIG. 7, the pin 34 is located at the distal end of the slot 35. Referring again to FIG. 8, the distal end 64 of the extension 16 is shown pulled back in the proximal direction. As a result, drive pin 86 is located at the proximal end of the slots 82 and 84, and the jaws 70 and 72 are in the closed position.

FIG. 9 shows the details of the extension 16. The extension 16 is comprised of three sections. These are the proximal end 26, the center span 22, and the distal end 64.

The spool 28 is retained on the proximal end 26 of the extension 16. The spool 28 slides over the proximal end of the extension 16 and rests against shoulder 100. A retaining clip 30 (see FIG. 1) slides into groove 98 to retain the spool 28 in place. Pin 34 (see FIG. 1) is pressed into hole 102 such that the end of pin 34 protrudes out one side of hole 102. O-ring seal 32 (see FIG. 1) rests within groove 24.

The center span 22 of the extension 16 is attached to the proximal end 26 of the extension 16 via hole 25 in the proximal end of the extension 16. The center span 22 is inserted into the hole 25 and permanently staked in place.

In a similar fashion, the center span 22 is staked to a clevis 104 located at the distal end 64 of the extension 16. The center span 22 is inserted in hole 103 in the clevis and permanently staked in place. The drive pin 86 (see FIG. 2) spans across a gap 106 in the clevis 104. This gap 106 provides clearance for the proximal ends of the jaws when the drive pin 86 engages the slots in the jaws.

FIG. 10 depicts the cleaning configuration of the tool assembly 12. In this configuration, the tool assembly 12 has been removed from the handle 14. The extension 16 has been pulled back within the sleeve 18 to a cleaning position. Pin 34 in the extension 16 is shown at the extreme proximal end of the slot 35 in sleeve 18. As shown in FIG. 10, in the cleaning position, the extension 16 is pulled back proximally far enough within the sleeve 18 to allow the O-ring seal 32 to move to the proximal side of the cleaning port 40.

Cleaning fluid is introduced into the tool assembly 12 from syringe 101 via the cleaning port 40. Because the extension 16 is in the cleaning position, the O-ring seal 32 prevents the cleaning fluid from traveling toward the proximal end of the tool assembly 12. The cleaning fluid enters the port 40 and travels down the tool assembly 12 and out to the jaw assembly 66. This effects a cleaning operation of the inside of the tool assembly 12. Also, the fluid running out of the distal end of the tool assembly 12 cleans the jaw assembly 66 as well.

It should also be noted that in this cleaning configuration, the drive pin 86 at the distal end of the extension 16 is no longer in engagement with the proximal ends of the jaws 70 and 72. The extension 16 has been drawn back toward the proximal end of the tool assembly 12 such that the pin 86 has disengaged the slots at the proximal ends of the jaws. The open ended slots 82 and 84 at the proximal ends of the jaws 72 and 70 facilitate the full translation of the extension to properly position the O-ring seal 32 during the cleaning operation.

Figure 11:
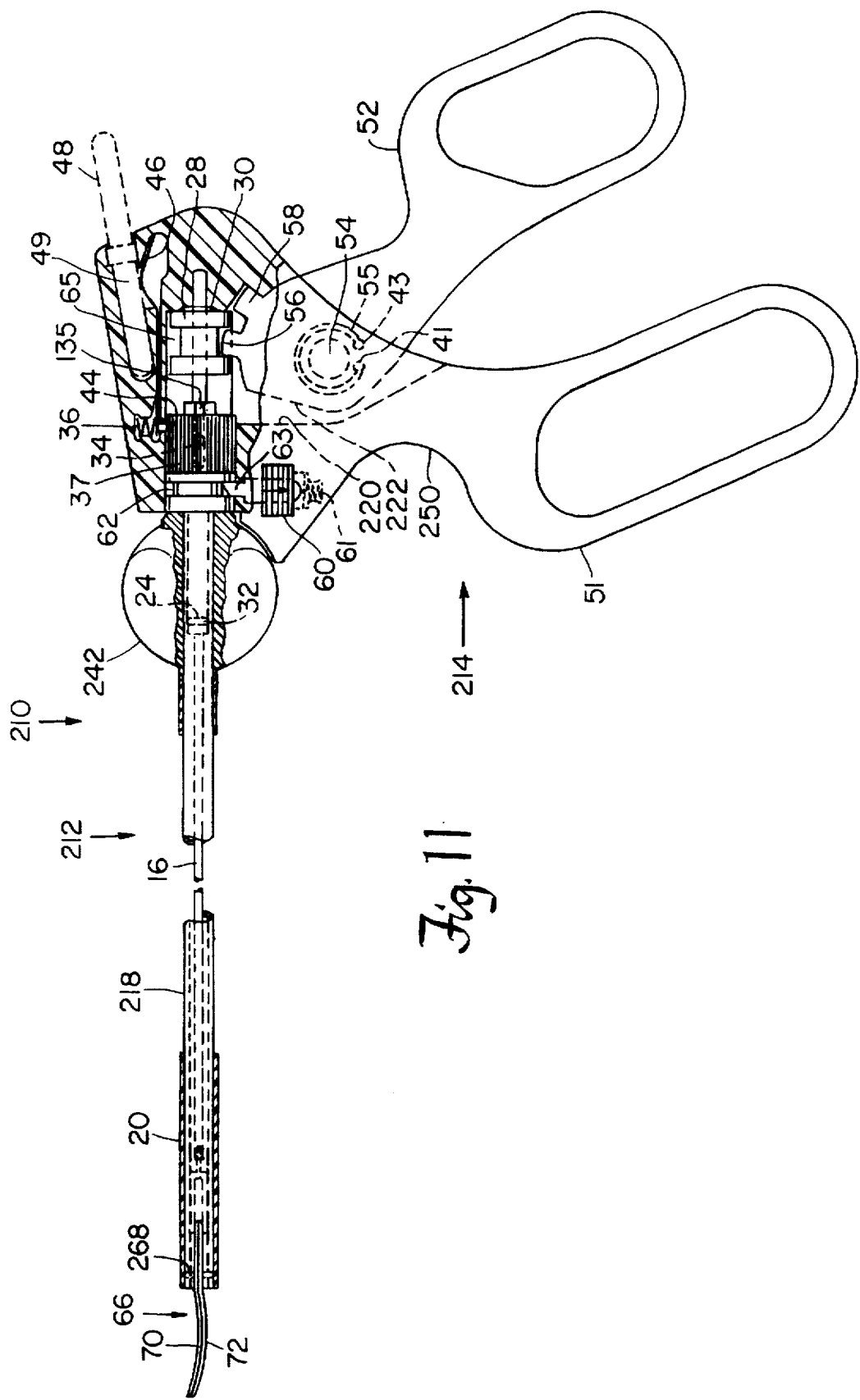
FIG. 11 is a schematic side elevational view of another embodiment of the surgical instrument of the present invention.

FIG. 11 depicts another embodiment 210 of the surgical instrument of the present invention. As with the prior embodiment, longitudinal translation of the extension 16 causes the jaws 70 and 72 to pivot between open and closed positions.

The sleeve 218 is retained within the handle 214 with the spring-loaded retaining knob 60 in engagement with retention groove 62 on rotating knob 42. Spring 61 biases the knob 60 toward the engagement position. Index rotator 37, detent 44, and spring 36 once again provide for indexed rotation of tool assembly 212. Electrical connections are provided in identical fashion to that of the previous embodiment.

Translation of the extension 16 within the sleeve 218 is initiated by rotation of the thumb loop or actuation trigger 52 about pivot 54. Tab 56 on actuation trigger 52 engages translation groove 65 on spool 28 to translate the extension 16 back and forth with rotation of the actuation trigger 52.

A difference between this embodiment and the previous embodiment is in the detachment and replacement of parts of the tool assembly 12. In this embodiment, only the sleeve 218 and jaw assembly 66 can be removed from the handle 214. The extension 16 remains permanently fixed within the handle 214.

To remove the sleeve 218 with jaw assembly 66, the user slides the spring-loaded retaining knob 60 out of engagement with the retention groove 62. Next, the user grasps the rotating knob 42 and pulls the sleeve 218 out of the port 17 of the handle 214. To allow the sleeve 218 to slide out of the handle 214 over the extension 16, the slot 135 in the sleeve 218 has an open proximal end. This allows pin 34, which is pressed into extension 16 as in the prior embodiment, to slide out of the slot 135 without interference.

In this embodiment, the extension 16 is permanently mounted within the handle 214. To retain the extension 16 within the handle 214, tab 56 is prevented from disengaging translation groove 65 in spool 28 by a limitation on the counter-clockwise rotation of the actuation trigger 52. This is effected by the interior structure of the base portion 250 of the handle 214. Specifically, a wall 220 is provided in the base 250 of the handle 214. As the actuation trigger 52 is rotated counter-clockwise, the wall 222 of the trigger interferes with wall 220. This prevents the actuation trigger 52 from rotating far enough to allow spool 28 to clear tabs 56 and 58 on the actuation trigger 52.

Cleaning is accomplished in this embodiment by simply introducing cleaning fluid into the proximal end of the sleeve 218 after it has been removed from the handle 214. Alternatively, as in the previous embodiment, the sleeve 218 may be provided with a cleaning port to allow the cleaning fluid to be introduced. The cleaning fluid runs down through the sleeve 218 and out the distal end of the sleeve 218 into the jaw assembly 66. The extension 16 is exposed for cleaning separately.

The jaw assembly 66 is mounted to the sleeve 218 via pivot pin 68. The jaws 70 and 72 pivot about the pivot pin 68 when actuated by the drive pin 86 at the distal end of the extension 16. When the jaw assembly 66 becomes dull or otherwise no longer usable, it can be replaced. The jaw assembly 66 is changed by simply installing a new sleeve 218 with attached jaw assembly 66 over the extension 216 and into the handle 214.

Figure 12:
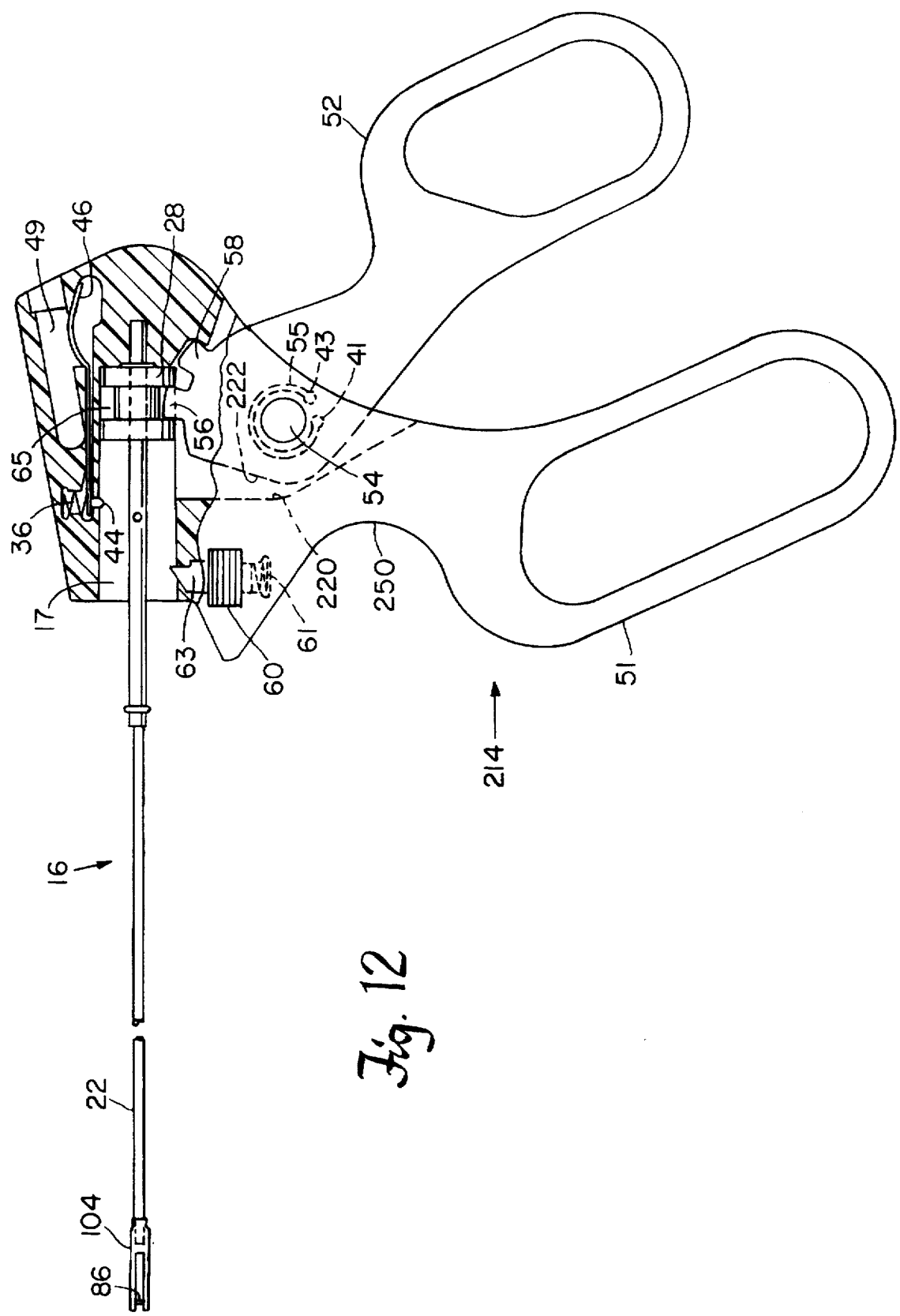
FIG. 12 is a schematic side elevational view of a handle assembly and extension of the surgical instrument of FIG. 11.

FIG. 12 depicts the surgical instrument 210 with the sleeve 218 and jaw assembly 66 removed. The extension 16 is retained within the port 17 of the handle 214. The tab 56 on actuation trigger 52 remains engaged with the translation groove 65 on spool 28. This engagement prevents the extension 16 from sliding out of the port 17. The actuation trigger 52 is prevented from rotating in the counter-clockwise direction by the interference between the wall surface 222 on the actuation trigger 52 and the wall surface 220 on the base 250 of the handle assembly 214.

The jaw assembly may also be removeably-attached to the distal end of the sleeve. This alternate means of jaw assembly attachment may be used in any embodiment of the surgical instrument. A jaw assembly is replaced by simply removing it from the sleeve and installing a new jaw assembly as described below.

The removable jaw assembly can be implemented by different approaches. In one embodiment, the distal end of the sleeve is made of an elastic material. A jaw assembly 66 is installed or removed from the sleeve by spreading its distal end open to provide clearance for the pivot pin 68 of the jaw assembly 66. When the jaw assembly 66 is in position within the sleeve, the distal end closes to hold the jaw assembly in place.

FIGS. 13 and 14 are cross-sectional views of the distal end of a sleeve 318 used in this first alternate jaw assembly attachment technique. A tubular insert 232 forms the end of the sleeve 318. The insert 232 is made of an elastic material such as a spring steel. Slots 230, 236, and 237 are cut into the wall of the insert by electronic discharge machining (EDM) or some other means. It should be noted that slots identical to slots 230, 236, and 237 are located on the opposite wall of the tubular insert 232. These are not seen in the cross-sectional elevational views of FIGS. 13 and 14.

Holes 234 and 235 are located in line on opposite sides of the slot 230. These holes are adapted to receive the pivot pin 68 of the jaw assembly 66 (not shown). The slot 230 is made sufficiently wide to provide clearance for the proximal ends of the jaws 70 and 72 when they are inserted into the end of the sleeve 318.

A jaw assembly 66 is installed on the distal end of the tubular insert 232 by spreading the end of the tubular insert 232 at the slot 230 as shown in FIG. 14. The ends of the slot 230 are spread sufficiently far apart to allow the pivot pin 68 to pass into the distal end of the tubular insert 232 and be engaged by holes 234 and 235. Slots 236 and 237 act together as a "living hinge" to allow the tubular insert 232 to spring open and closed without causing distortions in the material.

In FIG. 14, the tubular insert 232 is shown sprung open to receive the jaw assembly 66. The sleeve 318 is sprung open sufficiently wide to allow the pivot pin 68 of the jaw assembly 66 to pass into the slot 230. When the jaw assembly 66 is located in line such that the holes 234 and 235 can engage the pivot pin 68, the sleeve 318 is released to allow it to close over the pivot pin 68.

FIG. 15 is a cross-section of the distal end of the sleeve 318 showing the tubular insert 232 sprung open and receiving the jaw assembly 66. The end has been sprung sufficiently wide to allow the pivot pin 68 to pass through the slot 230. Also shown is the clevis 104 at the distal end of the extension 16. The clevis 104 carries the drive pin 86 at its distal end. Because the jaw assembly 66 has not been completely inserted into the insert 232, the drive pin 86 does not yet engage the proximal ends of jaws 70 and 72.

FIG. 16 depicts the distal end of the sleeve 318 after the jaw assembly 66 has been installed. The insert 232 has sprung closed again, the holes 234 and 235 engaging the pivot 68 of the jaw assembly 66. The drive pin 86 at the distal end of the clevis 104 is now shown to be engaging the slots in the proximal ends of the jaws 70 and 72. At this point, translation of the extension 16 toward the distal end of the sleeve 318, will cause drive pin 86 to drive the jaws 70 and 72 to the open position as previously described.

FIG. 17 is a perspective view of an insertion tool 300 in accordance with the present invention. The insertion tool 300 is shown loaded with a jaw assembly 66. The jaw assembly 66 rests in a housing or tray 302 of the insertion tool 300. The distal ends of the jaws rest against the inside wall 304 of the tray 302. The pivot 68 rests inside a slot 306 in the back side of the tray 302 (see FIG. 20). Levers 312 and 314 are pivotably mounted to the tray 302 via pivot pins 320 and 322 respectively.

The proximal ends 315 and 317 of levers 312 and 314 comprise wedges 324 and 326, respectively. The[] wedges 324 and 326 are shaped to engage the slots 230 on the tubular insert 232 at the distal end of the sleeve 318.

The levers 312 and 314 are pivotable about pivot pins 320 and 322 between an open position and a closed position. FIG. 17 depicts the levers in the closed position. During the insertion process, with the levers 312 and 314 in the closed position, the wedges 324 and 326 engage the slots 230 on the tubular insert 232 of the sleeve 318. The wedges engage the slots 230 to spread the end of the tubular insert 232 wide enough to allow the jaw assembly 266 to be inserted into the insert 232.

During the insertion process, after the jaw assembly 66 and insertion tool 300 have been inserted into the distal end of the sleeve 318, the levers 312 and 314 are pivoted to the open position. The wedges 324 and 326 are released from the slot 230. This allows the distal end of the tubular insert to close down over the pivot 68 in the jaw assembly 66.

After insertion is completed, the slot 306 in the tray 302 of the insertion tool 300 allows the insertion tool to be removed from the assembled sleeve 318 and jaw assembly 66.

FIGS. 18, 19, and 20 are perspective views showing three steps in the jaw assembly insertion process. FIG. 18 shows the distal end of the sleeve 318 without a jaw assembly 66 installed. The insertion tool 300 is shown with a jaw assembly 66 about to be installed on the sleeve 318. The non-conductive cover 20 is shown cut away so that details of the sleeve 318 can be viewed. The levers 312 and 314 are pivoted to the closed position.

The insertion process begins as the insertion tool 300 is moved in the direction of arrow 231. Wedges 324 and 326 engage slots 230 to spread open the end of the sleeve 318. The proximal end of the jaw assembly 66 slides into the distal end of the sleeve 318.

In FIG. 19, the insertion tool 300 and jaw assembly 66 have been inserted into the distal end of the sleeve 318 with the levers 312 and 314 in the closed position. The wedges 324 and 326 are engaged with slots 230. The sleeve has been spread apart at slots 230 and at the living hinge formed by slots 236 and 237. The holes 234 and 235 in the sleeve are spread far enough apart to allow the pivot pin 68 to pass between the holes 234 and 235. The holes 234 and 235 are aligned with the pivot 68 such that when the sleeve 318 is allowed to spring closed again, the jaw assembly 66 will be held within the sleeve 318 by the engagement of the holes 234 and 235 with the pivot 68.

FIG. 20 depicts the distal end of the sleeve 318 with the jaw assembly 66 installed. The sleeve 318 has closed down such that the pivot pin 68 of the jaw assembly 66 is retained in holes 234 and 235. The insertion tool 300 is shown in proximity to the sleeve 318 without a jaw assembly 66. The empty insertion tool 300 may be discarded or it may be retained for removal of a dull jaw assembly 66 from another sleeve 318.

To remove a jaw assembly 66 from the sleeve 318, the above process is reversed. An empty insertion tool 300 is inserted onto the distal end of the sleeve 318 with the levers 312 and 314 in the open position. The levers 312 and 314 are then pivoted to the closed position. Rear flat surfaces 327 and 329 on the levers (see FIG. 20) engage the proximal ends of the jaw assembly 66 to drag it from the sleeve 318. The wedges 324 and 326 spread the end of the sleeve 318 at the slots 230. When the sleeve 318 has been spread wide enough to allow the pivot pin 68 to clear the holes 234 and 235 in the sleeve 318, the insertion tool 300 and jaw assembly 66 are pulled out of the sleeve 318. The sleeve 318 springs closed and is ready for a new jaw assembly 66 to be inserted.

Figure 21:
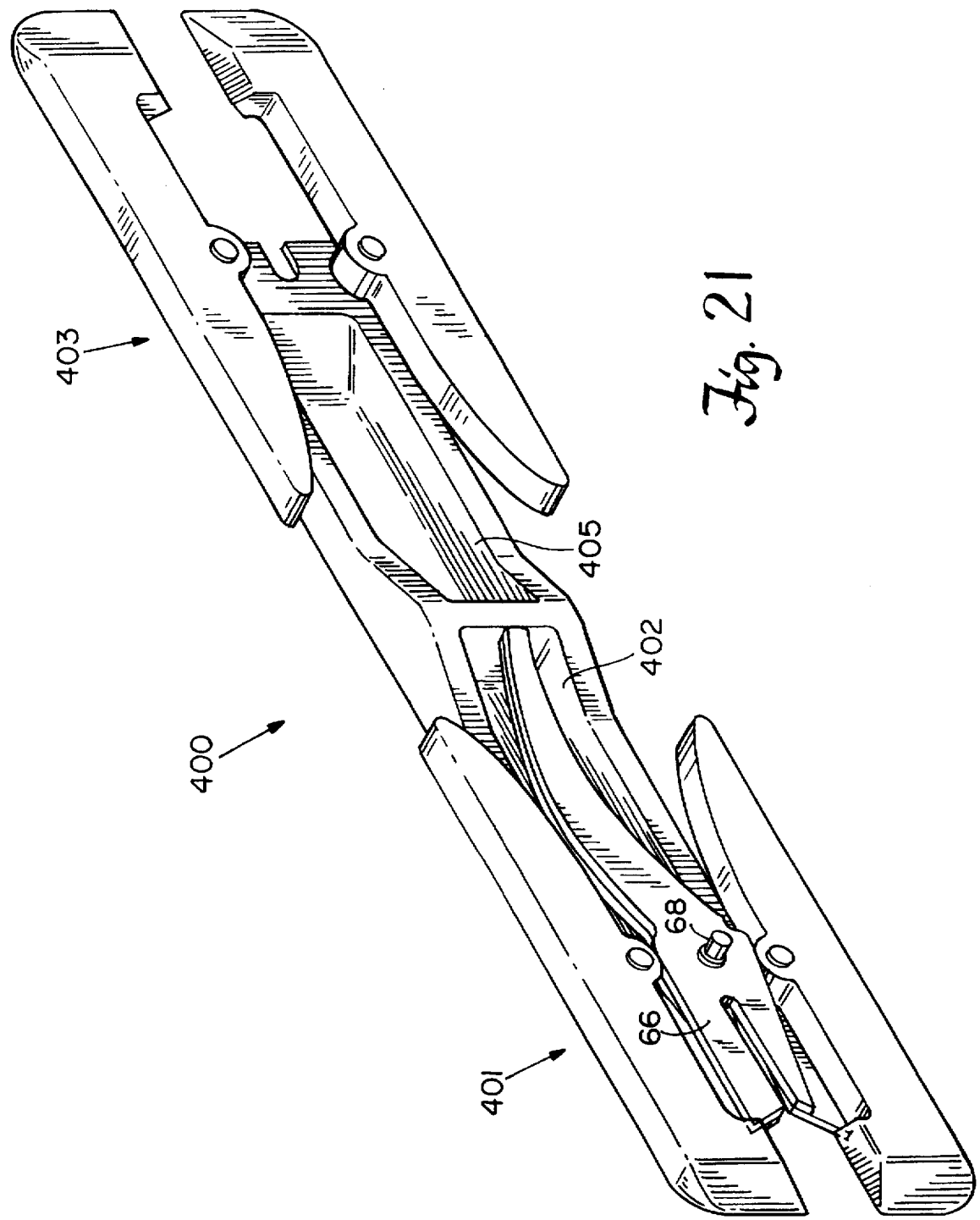
FIG. 21 is a perspective view of an embodiment of an insertion/removal tool in accordance with the present invention.

FIG. 21 is a perspective view of an insertion/removal tool 400 in accordance with the present invention. The insertion end 401 of the tool 400 is similar to the insertion tool 300 described above in connection with FIG. 17. A jaw assembly 66 is loaded in the housing 402 and is ready for insertion into a sleeve of a surgical tool assembly.

The removal end 403 of the insertion/removal tool 400 is identical to the insertion end 401, except that a jaw assembly is not loaded in the housing 405. The removal end 403 is used to remove a jaw assembly 66 from the end of a tool assembly as described above in connection with FIGS. 18-20.

The insertion/removal tool 400 is used to change jaw assemblies on a tool assembly. First, the removal end 403 is used to remove the old jaw assembly. After the old jaw assembly is removed, the insertion end 401 is used to install a fresh one. After the process is completed, the insertion/removal tool 400 with the old jaw assembly may be discarded.

Figure 36:
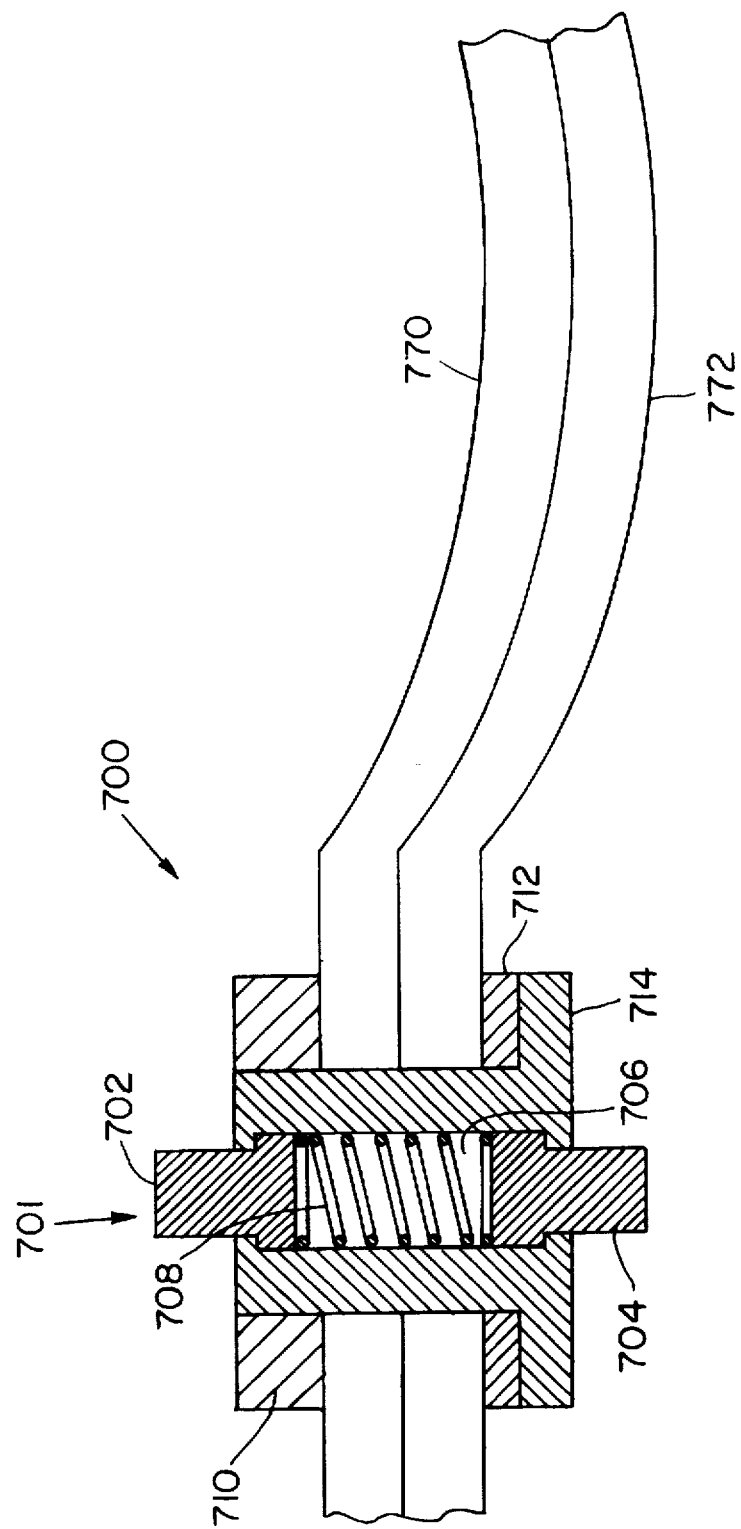
FIG. 36 is a cross-sectional view of an embodiment of a removable jaw assembly in accordance with the present invention.

FIG. 36 depicts another embodiment of a removable jaw assembly 700. In this embodiment, the jaws 770 and 772 are attached to each other by a compressible pivot 701. The pivot 701 holds the jaw assembly 700 in place in the distal end of tool assembly sleeve.

The compressible pivot 701 comprises two pivot ends 702 and 704 biased away from each other by partially compressed coil spring 708. The jaw assembly 700 is assembled by first installing pivot end 704 in the void 706 in tubular member 714. Next, the coil spring 708 is installed. The pivot end 702 is forced into the void 706 against the spring force of the coil spring 708. The pivot ends 702 and 704 and the spring 708 are then staked in place within the void 706 of the tubular member 714.

The tubular member 714 is then inserted through a spring washer 712 and then through holes in the jaws 770 and 772. A flange 710 is pressed onto the tubular member 714 to hold the jaw assembly 700 together. The spring washer 712 maintains compression between the jaw blades 770 and 772 to ensure proper operation.

To install the jaw assembly 700 into a sleeve, the pivot ends 702 and 704 are compressed toward each other. The jaw assembly 700 is then made to slide into the distal end of the sleeve. When the ends 702 and 704 come into alignment with holes through opposite walls of the sleeve, they snap into engagement with the holes to hold the jaw assembly 700 in place. To remove the jaw assembly 700, the pivot ends 702 and 704 are compressed toward each other sufficiently to allow them to clear the holes in the walls of the sleeve. The jaw assembly 700 is then caused to slide out of the sleeve.

The handle assembly can also be provided in a dual-port configuration as described in U.S. patent application Ser. No. 07/903,162 of which this application is a continuation-in-part. In this configuration, pivoting of the trigger provides translation motion in both of the two ports. The tool assembly can be inserted into either of the ports. When the trigger is pivoted with respect to the handle, the jaws are pivoted between open and closed positions.

The handle assembly of the present invention can also be provided in a rotatable-port or universal-port configuration. The rotatable-port handle assembly comprises a base or housing which has a single port in which a tool assembly 12 is retained and actuated. A finger loop and a thumb loop or actuation trigger are pivotably mounted to the housing. As in the embodiments previously described, relative rotational motion between the thumb loop and the finger loop provides translational motion to the port to actuate the tool assembly.

Figure 22:
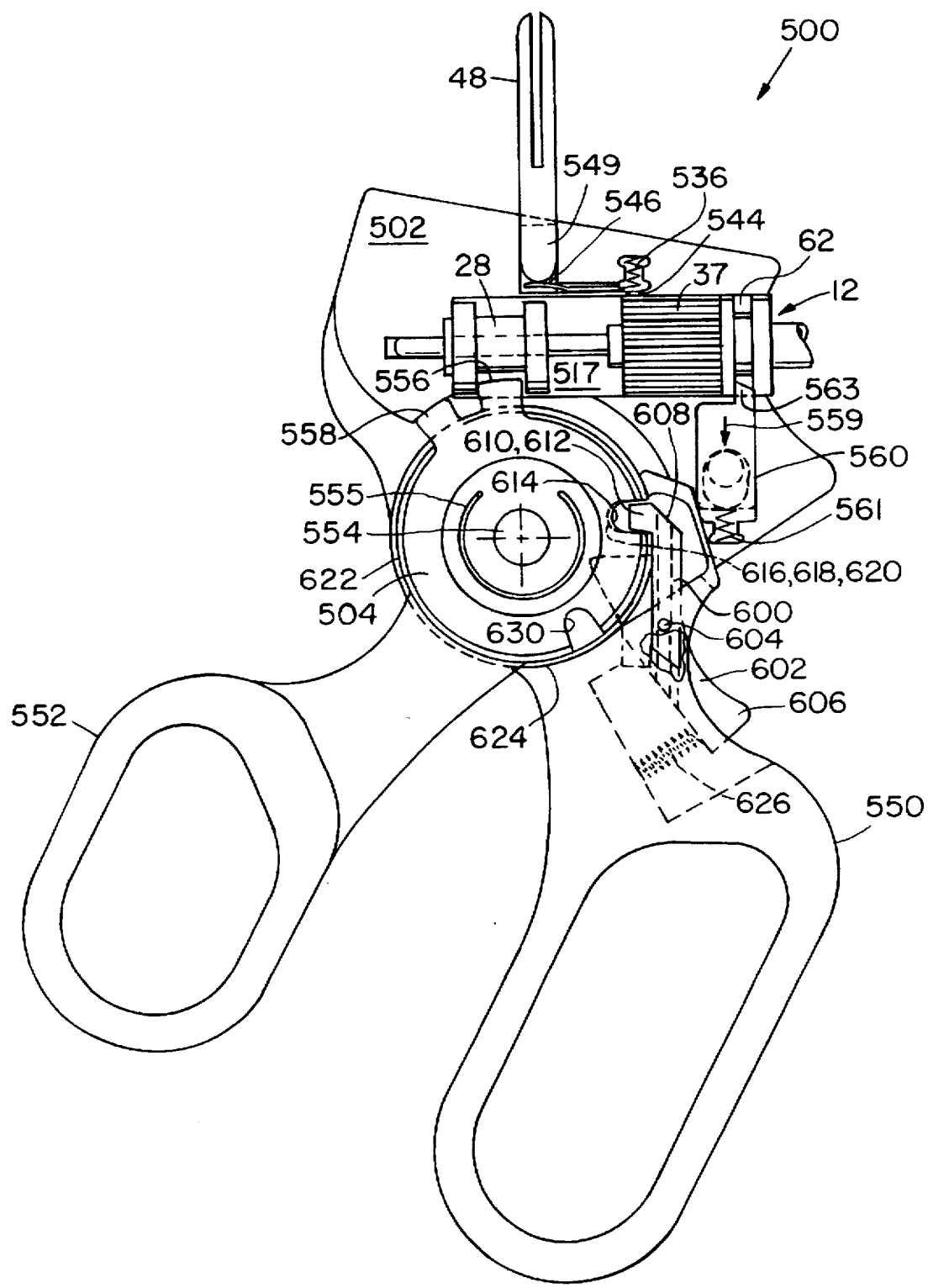
FIG. 22 is a schematic side elevational view of a rotatable-port embodiment of a handle assembly in accordance with the present invention.

The rotatable-port handle 500 is operable in either of two configurations—a pistol configuration and a scissor configuration. The pistol configuration is depicted in FIG. 22. In the pistol configuration, the finger loop 550 is fixed to the housing 502 in the orientation shown. The thumb loop or actuation trigger 552 is pivotable relative to the finger loop 550 to actuate the tool assembly 12.

Figure 26:
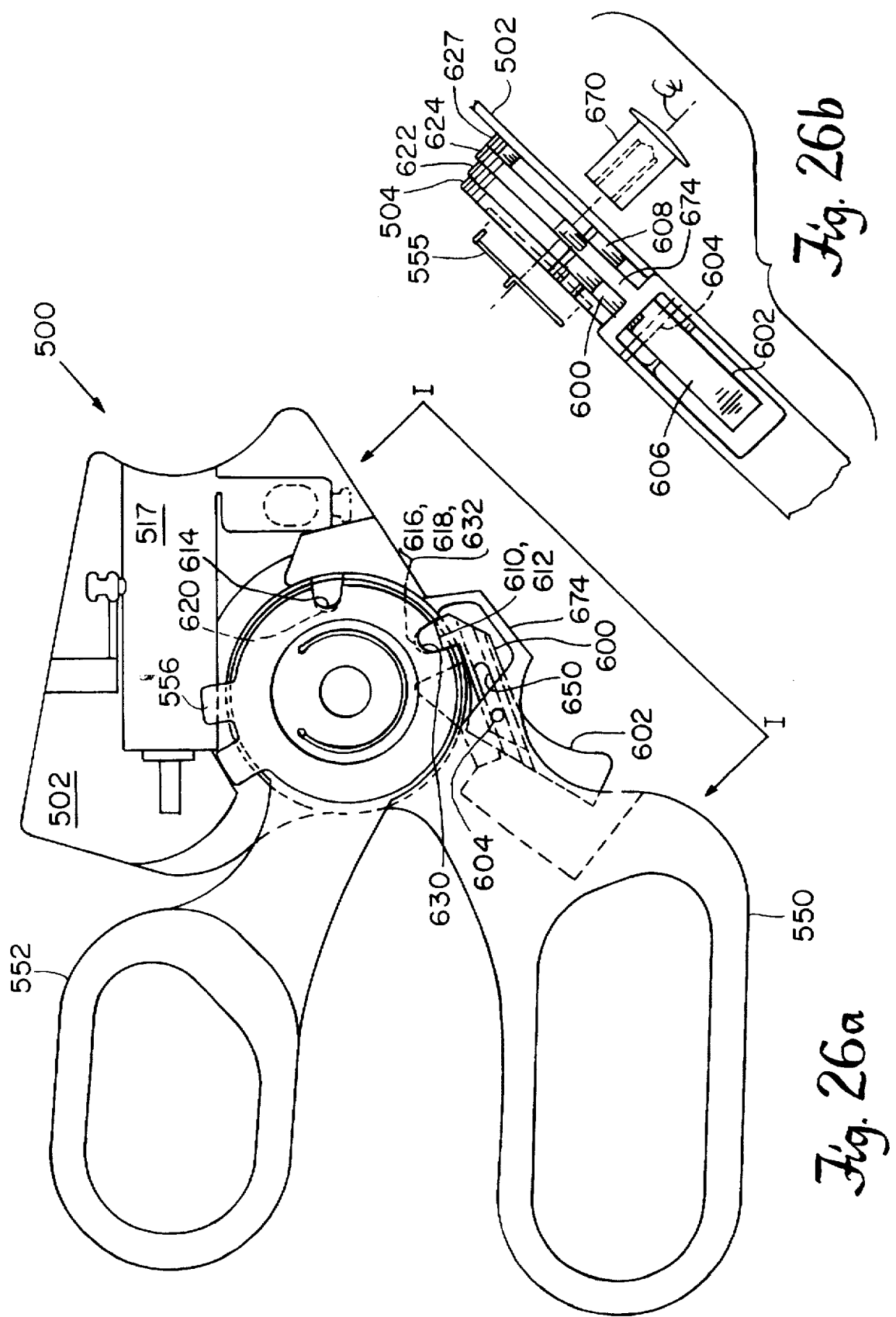

The scissor configuration is shown in FIG. 26a. The finger loop 550 is fixed to the housing 502 in the orientation shown. Once again, the thumb loop 552 is pivotable relative to the finger loop 550 to actuate the tool assembly.

The finger loop 550 and thumb loop 552 can be readily positioned in either the pistol or scissor configuration. In its closed or engagement position, a release trigger 602 locks the handle assembly 500 in either of the positions. When it is desired to change positions, the release trigger 602 is rotated to its open position to release the handle 500 from its present configuration. The thumb loop 552 and finger loop 550 are then rotated until the release trigger 602 locks them in the new position.

FIG. 24 shows the interaction of the parts of the rotatable-port handle assembly 500. The housing 502 and top cover 503 come together to form the port 517 for a tool assembly (not shown). The housing 502 is formed with a housing disk 627. The housing disk 627 has a pistol configuration notch 620 and a scissor configuration notch 632 formed in its outer circumference.

The finger loop 550 is formed with a finger disk 624 which lays over the housing disk 627 when the handle 500 is assembled. The release trigger 602 is pivotably mounted to the finger loop 550. The trigger key 612 engages finger notch 618 on the finger disk 624 and notch 620 on the housing disk 627 when the handle is in the pistol configuration. In the scissor configuration, the trigger key 612 engages notches 618 and 632.

A slide member 600 is coupled to the release trigger 602. The slide member 600 is permitted to slide along the release trigger 602 guided by a rail 646 on the release trigger 602 mated with a groove 648 in the slide member 600. The slide member 600 has a slide key 610 which does not engage the notch 618 on the finger disk 624. So, even when the trigger key 612 is engaged with notch 618, the slide member 600 is free to slide independent of the release trigger 602.

The thumb loop 552 is formed with a thumb disk 622 having a notch 616 formed in its outer surface. The thumb disk 622 lays over the finger disk 624 in the handle 500, and a drive cog 504 lays over the thumb disk 622. The drive cog 504 is formed with a tab 556 which actuates the tool assembly when the drive cog 504 is assembled in the instrument.

In both the pistol and the scissor configurations, the drive cog 504 is fixed to the thumb disk 622. When the thumb loop 552 is rotated with respect to the finger loop 550, the drive cog 504 rotates with it to actuate the tool assembly. The thumb disk 622 and drive cog 504 are held together by the slide key 610. The slide key 610 engages thumb notch 616 and one of the notches 614 and 630 on the drive cog 504. In the pistol configuration, the slide key 610 engages notch 616 and the drive cog pistol configuration notch 614. In the scissor configuration, the slide key 610 engages notch 616 and the scissor configuration notch 630.

During normal operation, the release trigger 602 is in its closed position. In the pistol configuration, for example, the trigger key 612 engages notches 618 and 620, and the slide key 610 engages notches 614 and 616. The thumb loop 552 is rotated relative to the finger loop 550 to actuate a tool assembly. As the thumb loop 552 rotates, the slide member 600 slides along the release trigger 602, carried by the engagement between the notches 614, 616 and the slide key 610. The slide key 610 fixes the drive cog 504 to the thumb loop 552. As the thumb loop 552 rotates, the tab 556 translates within the port 517 to actuate the tool assembly.

FIG. 22 is a side elevational view of the rotatable-port or universal-port handle assembly 500 in accordance with the present invention. The handle assembly 500 comprises the housing or base 502 having the port 517 in which a tool assembly 12 is retained and actuated in accordance with the foregoing description. The thumb loop or actuation trigger 552 and the finger loop 550 are pivotably mounted to the housing 502 by pivot 554. The thumb loop 552 and finger loop 550 are pivotable relative to each other and relative to the housing 502.

The drive cog 504 is pivotably mounted to the finger loop 550, the thumb loop 552 and the housing 502 by pivot 554. The drive cog 504 comprises the tab 556 on its outer diameter which engages the translation groove 65 in the spool 28 of a tool assembly 12 as previously described. As the drive cog 504 is caused to rotate about pivot 554, the spool 28 is translated back and forth to actuate the tool assembly 12.

The release trigger 602 is pivotably mounted to the finger loop 500 by pivot 604. A slide member 600 is slidably mounted on the release trigger 602. The release trigger 602 comprises a depression end 606 and a key end 608. The trigger key 612 is located at the key end 608 of the release trigger 602. The slide key 610 of the slide member 600 is shown in FIG. 22 in alignment with the trigger key 612. Thus, in the elevational view, the trigger key 612 cannot be seen because it is behind the slide key 610 of the slide member 600.

The slide key 610 engages notch 614 on the outer surface of the drive cog 504 and notch 616 on the thumb disk 622 of the thumb loop 552 during actuation of the tool assembly 12. This eliminates rotational movement between the drive cog 504 and the thumb loop 552. Thus, when the thumb loop 552 is rotated about pivot 554, the drive cog 504 is carried with it. As the drive cog 504 rotates, tab 556 causes the spool 28 to translate longitudinally within the port 517 to actuate the tool assembly 12.

The finger loop 550 is prevented from rotating with respect to the housing 502 by the release trigger 602. The trigger key 612 on the release trigger 602 engages notch 618 on the finger disk 624 of the finger loop 550 and notch 620 on the housing disk 627 (see FIG. 24) on the housing 502. Thus, while a tool assembly 12 is being actuated, the finger loop 550 and the housing 502 are in a fixed relationship to each other. The interactions and relationships among the various disks, notches, and keys will be described below in greater detail.

The release trigger 602 is spring loaded. Coil spring 626 biases the release trigger 602 in the counter-clockwise rotational direction toward the closed or engagement position depicted in FIG. 22. Pressing the depression end 606 of the release trigger 602 causes the release trigger 602 to rotate in the clockwise direction about pivot 604 against the biasing force of coil spring 626. Trigger key 612 comes out of engagement with notches 618 and 620. Slide member 600 is carried with the release trigger 602 such that the slide key 610 comes out of engagement with notches 614 and 616. When the trigger 602 is released, if the notches line up with their corresponding keys, the coil spring 626 forces the trigger 602 to pivot such that the keys drop into engagement with the notches.

The handle assembly 500 is operable in two possible configurations, the pistol configuration shown in FIG. 22 and a scissor configuration shown in FIGS. 26a and 26b. The instrument may be changed from one configuration to the other by rotating the finger loop 550 and thumb loop 552 with respect to the housing 502 and the drive cog 504. As an illustration, the process of rotating from the pistol configuration to the scissor configuration will be described.

The rotation process is carried out by depressing the release trigger 602 to release the drive cog 504 and the various disks from each other. Next, the thumb loop 552 and finger loop 550 are rotated to the new position while the housing 502 and drive cog 504 remain stationary. When the new position is reached, the release trigger 602 closes. The slide key 610 on the slide member 600 drops into engagement with the notch 616 on the thumb disk 622 and a scissor configuration notch 630 on the drive cog 504 to lock the two together. At the same time, the trigger key 612 engages the notch 618 on the finger disk 624 and a scissor configuration housing disk notch 632 (see FIG. 24) to lock the handle 500 in the configuration. The details of the rotation processes will be described below in connection with more detailed drawings.

The tool assembly 12 is retained within the port 518 in a manner similar to that described for the other embodiments. The tapered end 563 of spring-loaded knob 560 engages the retention groove 62 in the tool assembly 12. A coil spring 561 biases the knob 560 toward the engagement position. When a tool assembly 12 is being removed, the knob is forced to slide in the direction indicated by the arrow 559 against the biasing force of coil spring 561 until the end 563 of the knob 560 slides out of engagement with the retention groove 62. When a tool assembly 12 is being installed in the port 517, the taper on the end 563 of the knob 560 allows the knob 560 to be forced out of the way as the tool assembly slides into the port 517. The end 563 of the knob 560 snaps into engagement with the retention groove 62 as the tool assembly 12 slides all the way back into the port 517.

A torsion spring 555 couples the drive cog 504 to the top cover 503 of the housing 502 (see FIG. 24). The function of the torsion spring 555 is similar to that of the torsion spring 55 in the other embodiments. The spring 555 biases the rotation of the drive cog 504 in a clockwise direction to locate the tab 558 within the port 517 during installation of a tool assembly 12 to ensure proper installation.

The rotatable-port handle assembly 500 also provides for electrical connections to the tool assembly 12 via electrical connection port 549. An electrical connector 48 is inserted in port 549. The spring clip 546 provides an electrical connection from the connector 48 to the index rotator 37 fixed to the tool assembly 12. Coil spring 536 applies force to detent 544. The detent 544 rides on the outer surface of index rotator 37 to provide indexed rotation of the tool assembly 12. The spring clip 546 is squeezed between the spring 536 and the detent 544. Thus, the electrical connection is provided to the tool assembly 12.

Figure 23:
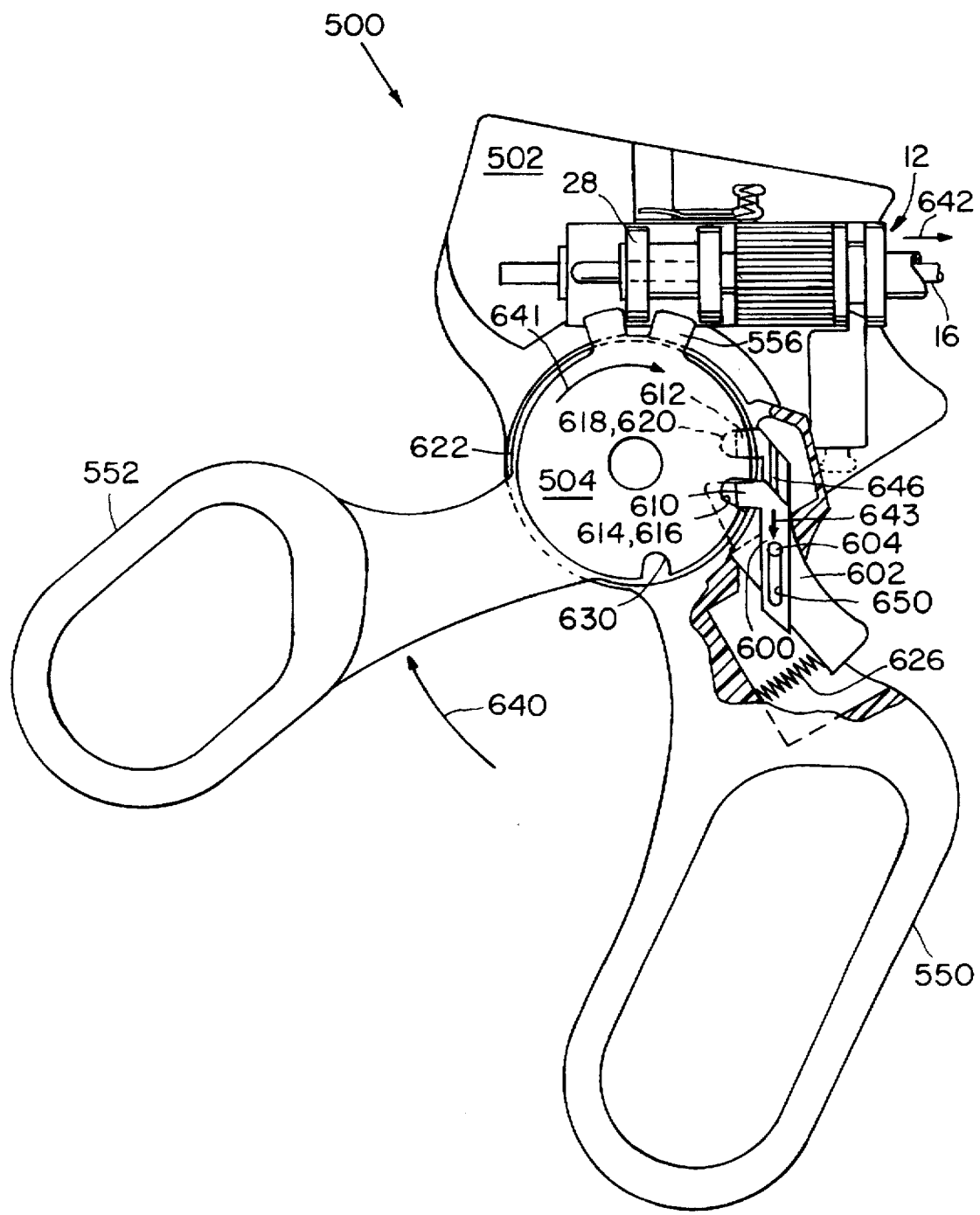
FIG. 23 is a schematic side elevational view of the rotatable-port handle assembly of FIG. 22 showing the tool actuation process.

FIG. 23 depicts the operation of the handle assembly 500 during actuation of the tool assembly 12. When the thumb loop 552 is rotated in the direction indicated by arrow 640, the thumb disk 622 and the drive cog 504 rotate in the direction indicated by the arrow 641. Tab 556 imparts translational motion to the spool 28 and extension 16 of the tool assembly 12 as indicated by arrow 642 to actuate the tool assembly 12.

As shown in FIG. 23, the slide key 610 of the slide member 600 has engaged notch 614 in the drive cog 504 and notch 616 in thumb disk 622. Consequently, the drive cog 504 rotates with the thumb loop 552. Also, the trigger key 612 on the release trigger 602 has n engaged notch 618 on the finger disk 624 of the finger loop 550 and the notch 620 in the housing disk 627. Therefore, the finger loop 550 is held stationary with respect to the housing 502.

FIG. 23 also illustrates the operation of the release trigger 602 and slide member 600 while the tool assembly is being actuated. As the thumb loop 552 rotates in the direction shown by arrow 640, the slide member 600 is carried along the release trigger 602 via the interference between the walls of the notches 614 and 616 and the slide key 610. The slide member 600 slides along the release trigger 602 guided by slide rail 646 in the trigger release 602 and a meshing slide groove 648 in the slide member 600 (see FIG. 33b). Also, the slot 650 in the slide member 600 slides along pivot 604. The slot 650 can serve to limit the travel of the slide member 600.

FIG. 24 is a schematic exploded view of the handle assembly 500 of the present invention. The housing 502 comprises the port 517 for a tool assembly. Also shown is the housing disk 627. In this embodiment, the housing disk 627 is an integral part of the housing 502. The housing 502 is molded with the disk 627 formed as shown.

The housing disk 627 comprises a notch 620 and a notch 632 on its outer diameter. Depending upon the configuration, the trigger key 612 on the release trigger 602 meshes with one of these notches. If the handle 500 is in the pistol configuration (FIG. 23), the trigger key 612 meshes with notch 620. In the scissor configuration (FIG. 26a), the trigger key 612 meshes with notch 632.

The finger loop 550 is shown with the release trigger 602 attached at pivot 604. The slide member 600 is shown slideably attached to the release trigger 602. The slide member 600 slides along the release trigger 602 guided by the mating rail 646 in the release trigger 602 and groove 648 in the slide member 600. Pivot 604 passes through slot 650 in the slide member 600. As described above, the groove 650 and pivot 604 guide the sliding of the slide member 600 as well as limit the extent of its travel.

The slide key 610 of the slide member 600 is shown aligned with the trigger key 612. However, this need not be the case. In the figure, the release trigger 602 is in the closed position so that the trigger key 612 meshes with notch 618 in the finger disk 624. But, slide key 610 in the slide member 600 does not mesh with the notch 618. Therefore, when the thumb loop 552 and finger loop 550 rotate relative to each other, the slide member 600 is free to slide independent of the release trigger 602.

The back surface 623 of the finger disk 624 contacts the front surface 629 of the housing disk 627 when the handle 500 is assembled. Pivot hole 652 in the housing disk 627 is aligned with pivot hole 654 in the finger disk 624. In the orientation shown, the finger loop 550 is positioned such that, when the housing is assembled, the trigger key 612 will mesh with notch 620 in the housing disk 627 when the release trigger 602 is in the closed position. With the trigger key 612 in notch 620, the handle 500 is in the pistol configuration. To change to the scissor configuration, the trigger 602 is depressed to disengage the trigger key 612 from the notches 618 and 620. Next, the finger loop 550 is rotated in the clockwise direction until notch 618 in the finger disk 627 is aligned with notch 632 in the housing disk 627. The release trigger 602 then closes; the trigger key 612 falls into engagement with the notches 618 and 632 to lock the handle 500 in the scissor configuration.

The back surface 621 of the thumb loop 552 contacts the front surface 625 of the finger-loop 550 when the handle 500 is assembled. Pivot hole 656 in the thumb disk 622 is aligned with pivot hole 654 in the finger disk 624. The thumb loop 552 is shown oriented such that the notch 616 in the thumb disk 624 is aligned with notches 618 and 620 in the finger disk 624 and housing disk 627, respectively. As a result, when the handle 500 is assembled the slide key 610 will engage the notch 616 with the keys 610 and 612 aligned as shown.

The back surface 660 of the drive cog 504 contacts the front surface 662 of the thumb disk 622 when the handle 500 is assembled. Pivot hole 656 in the thumb disk 622 is aligned with pivot hole 658 in the drive cog 504. In the orientation shown in FIG. 24, pistol notch 614 on the drive cog 504 is aligned with notch 616 on the thumb disk 622. With the release trigger 602 in the closed position as shown, the slide key 610 will engage notches 614 and 616 to lock the drive cog 504 in fixed rotational relation with thumb disk 622 in the pistol configuration.

Note that in this configuration, the tab 556 on the drive cog 504 is oriented substantially vertically. Therefore, when the handle 500 is assembled, the tab 556 will extend into the port 517 to drive a tool assembly 12. When the handle 500 is changed to the scissor configuration, the drive cog 504 must retain essentially the same rotational orientation as that shown in FIG. 24. This orientation keeps tab 556 protruding into the port 517 to drive a tool assembly 12 in either configuration. Thus, when the rotation process is carried out, the release trigger 602 is depressed to disengage trigger key 612 from the finger disk notch 618 and pistol configuration notch 620 on the housing disk 627. At the same time, slide key 610 disengages thumb disk notch 616 as well as the pistol configuration notch 614 on the drive cog 504. The thumb loop 552 and finger loop 550 are then rotated together to the scissor position while the drive cog 504 and housing disk 627 remain substantially stationary.

When the notch 618 on the finger disk 624 is aligned with the scissor configuration notch 630 on the housing disk 627, the trigger key 612 falls into engagement with the notches 618 and 632 to lock the finger loop 550 to the housing disk 627 in the scissor position. When the notch 616 on the thumb disk 622 is aligned with the scissor configuration notch 630 on the drive cog 504, the slide key 610 falls into engagement with the notches 616 and 630 to lock the thumb disk 622 to the drive cog 504 in the scissor configuration. The rotation process is carried out with a tool assembly 12 installed in the port 517. Frictional forces inherent in the tool assembly inhibit rotation of the drive cog 504 when the trigger is in the release or open position.

Torsion spring 555 couples the drive cog 504 to the top cover 503 of the handle 500. One end 666 of the spring 555 is inserted into a hole 664 in the drive cog 504. The other end 668 of the spring 555 is inserted in a hole in the back side of the cover 503 (not shown). The torsion spring 555 tends to bias rotation of the drive cog 504 and thumb loop-552 in the clockwise direction. This clockwise bias aids during installation of a tool assembly 12 into the port 517. When the port 517 is empty, tab 558 on the drive cog 504 is rotated into the port 517. During insertion of a tool assembly, the tab 558 ensures that tab 556 will rotate into proper engagement with the tool assembly.

A pivot nut 670 passes through the pivot holes 652, 654, 656, 658 in the disks and the drive cog to hold them in position. A pivot screw 672 threads into the pivot nut 670 through the cover 503, the drive cog 504, and the disks to hold the handle assembly 500 together.

As previously described, in either the pistol configuration or the scissor configuration, the handle assembly 500 actuates a tool assembly 12 by relative rotational motion between the finger loop 500 and thumb loop 552. With the release trigger 602 in the closed position, the finger loop 550 is stationary with respect to the housing 502 and therefore also with respect to a tool assembly in the port 517. Tab 556 engages the tool assembly in the port 517. As the thumb loop 552 is rotated, tab 556 on the drive cog 554 is carried back and forth within the port 517 to actuate the tool assembly.

Thus, while a tool assembly 12 is being actuated by the handle assembly 500, the thumb loop 552 and drive cog 504, coupled together by the slide key 610, rotate with respect to the finger loop 550 and housing 503, coupled together by trigger key 612. This independent rotation is facilitated by the sliding motion between the release trigger 602 and the slide member 600. As the thumb loop 552 and drive cog 504 rotate, slide member 600 slides along the release trigger 602. The slide member 602 is caused to slide by the engagement of the slide key 610 with the thumb loop notch 616 and either the pistol configuration notch 614 or the scissor configuration notch 630 on the drive cog 504. As it slides, the slide member 600 is guided by the mating slide rail 646 on the release trigger 602 and slide groove 648 on the slide member 600.

In FIG. 24, the handle assembly 500 is shown in the tool-assembly-closed position. That is, the relative rotational orientation of the finger loop 550 to the thumb loop 552 is such that the tab 556 is pulled back within the port 517 to close the tool assembly jaws as previously described. The thumb loop 552 is rotated as far as possible in the counter-clockwise direction. This can be seen by the positions of the notches 614, 616, 618, and 620 and the position of the slide member 600 with respect to the release trigger 602. The notches are all in alignment, and the slide member 600 is at the limit of its travel at the top of the release trigger 602. Thumb loop 552 will not rotate further in the counterclockwise direction because groove 650 in the slide member 600 and pivot 604 will prevent the slide member 600 from sliding further along the release trigger 602. Clockwise rotation of the thumb loop 552 to open tool jaws is not inhibited by the slide member 600 because slot 650 and pivot 604 will allow the slide member 600 to slide down the release trigger 602.

Figure 25:
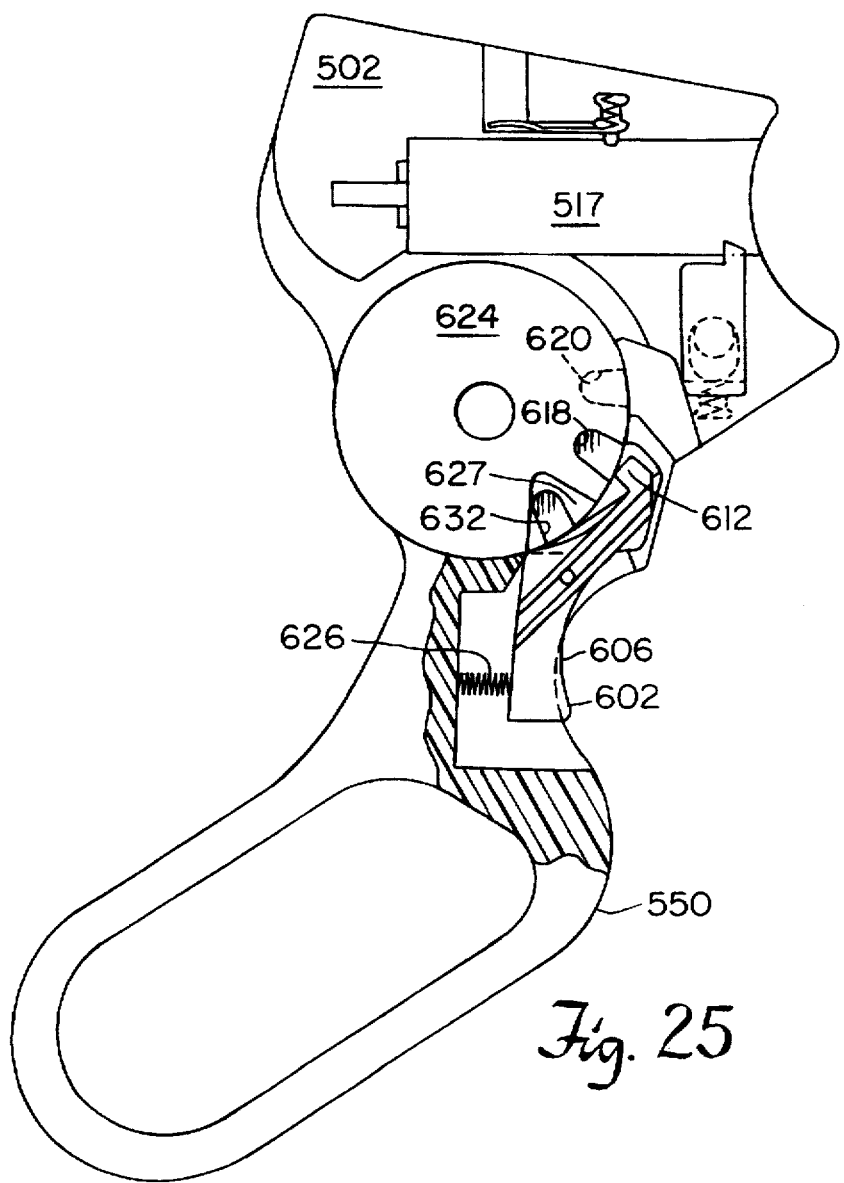
FIG. 25 is a schematic side elevational view of the housing and finger loop of the rotatable-port handle assembly.

FIG. 25 is a schematic side elevational view of the housing 502 and the finger loop 550 of the handle assembly 500. The housing 502 and finger loop 550 are shown during the rotation process. The thumb loop 552 and the drive cog 504 are removed in order to clearly illustrate the rotation process as it pertains to the finger loop 550 and the housing 502. Also, the slide key 600 has been removed from the release trigger 602.

In FIG. 25, the finger loop 550 is shown approximately midway between the pistol configuration and the scissor configuration. For illustration purposes only, it will be assumed that the finger loop 550 is being moved from the pistol configuration to the scissor configuration. However, it will be understood that the figure also illustrates the reverse process.

The depression region 606 has been depressed against coil spring 626 such that the release trigger 602 is rotated into the open or release position. The trigger key 612 has come out of engagement with the pistol configuration notch 620 on the housing disk 627 as well as the notch 618 on the finger disk 624.

During the rotation of the finger loop 550, the trigger key 612 rides along the outer surface of the housing disk 627. Thus, pressure need not be maintained on the depression region 606 of the release trigger 602 to maintain it in the release position. As the finger loop 550 is rotated closer to the scissor position, the finger loop notch 618 and the trigger key 612 approach the scissor configuration notch 632 on the housing disk 627. When the finger notch 618 is aligned over the scissor configuration notch 632, the trigger key 612 is allowed to fall into engagement with both notches, thus fixing the finger loop 550 and the housing 502 in the scissor configuration.

To rotate the finger loop 550 back to the pistol configuration, the release trigger 602 is depressed to release the finger disk from the housing disk. The finger loop 550 is then rotated toward the pistol configuration. The trigger key 612 rides on the circumference of the housing disk 627. When the notch 618 lines up with pistol configuration notch 620 on the housing disk 627, the trigger key 612 falls into the notches, locking the finger loop 550 and the housing 502 in the pistol configuration.

FIGS. 26a and 26b depict the handle assembly 500 in the scissor configuration. The finger loop 550 and thumb loop 552 have been rotated to new positions relative to the housing 502 and drive cog 504. The tab 556 on the drive cog 504 remains in a substantially vertical orientation such that it protrudes into the port 517.

The release trigger 602 is shown in the closed position such that the handle 500 is locked in the scissor configuration. Slide key 610 is shown aligned with trigger key 612 and pivot 604 is shown at the end of slot 650 in the slide member 600. Thus, once again, the thumb loop 552 is rotated as far as possible in the counter-clockwise direction relative to the finger loop 550 such that the tab 556 is pulled back as far as possible within the port 517.

In the scissor configuration as shown, the trigger key 612 engages finger notch 618 and the scissor configuration notch 632 on the housing disk 627. Slide key 610 engages thumb notch 616 and the scissor configuration notch 630 in the drive cog 504. The pistol configuration notches 614 in the drive cog and 620 in the housing 502 are not engaged by either of the keys.

In the scissor configuration, actuation of a tool assembly is performed in the same manner as in the pistol configuration. Thumb loop 552 is rotated with respect to finger loop 550. The finger loop 550 is held stationary with respect to the housing 502 by trigger key 612. As the thumb loop 552 rotates, the drive cog 504 is carried with it because the slide key 610 locks the drive cog 504 to the thumb disk 622. As the drive cog 504 rotates, the tab 556 translates within the port 517 to actuate a tool assembly.

FIG. 26b is a schematic view taken along line A—A of FIG. 26a. The housing 502 comprises housing disk 627. The finger disk 624 is on top of the housing disk 627, and the thumb disk 622 is on top of the r finger disk 624. The drive cog 504 is on top of the thumb disk 622. The torsion spring 555 is shown exploded out of the figure for clarity.

Each of the disks and the drive cog 504 has a different diameter. Specifically, in this embodiment, the disks decrease in diameter in the direction away from the housing 502. The differing diameters work in conjunction with the surfaces of the keys 610 and 612 to control the process of rotation between the pistol configuration and the scissor configuration. The sequence in which the keys drop into engagement with the notches on the disk is controlled to ensure that the rotation process is properly carried out. This sequencing will be described below in detail.

FIG. 26b also shows the release trigger 602 mounted on pivot 604. The depression end 606 and the key end 608 are on opposite sides of the pivot 604. Slide member 600 is also shown. A guard 674 is an integral part of the finger loop 550. It prevents foreign objects from interfering with the mechanism of the trigger 602, slide member 600, and notches.

Figure 27:
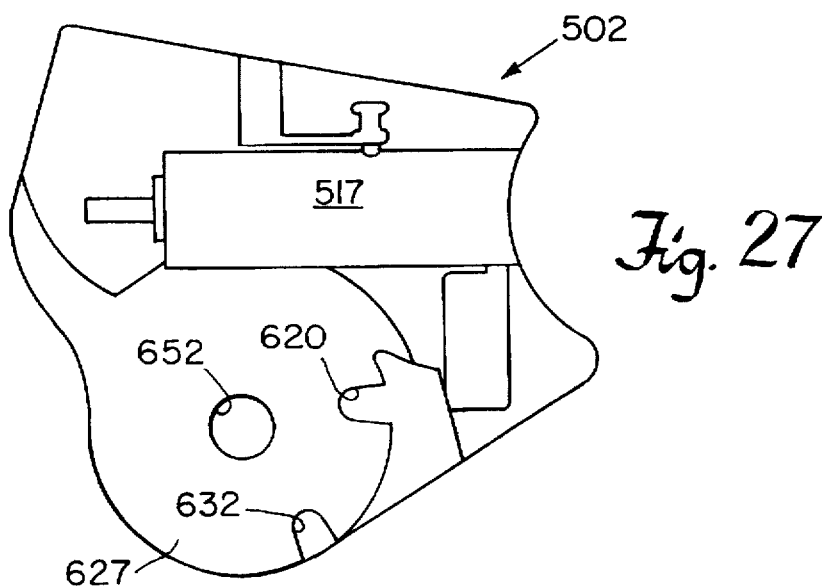
FIG. 27 is a schematic elevational view of the housing of the rotatable-port handle assembly.

FIG. 27 is a schematic elevational view of the housing 502 of the handle assembly 500. The housing 502 includes half of the tool assembly port 517 and the integral housing disk 627. Pivot hole 652 passes through the housing at approximately the center of the housing disk 627. The housing disk 627 comprises a pistol configuration notch 620 and a scissor configuration notch 632 both of which are engageable by the trigger key 612 to lock the housing disk 627 to the finger disk 624.

Figure 28:
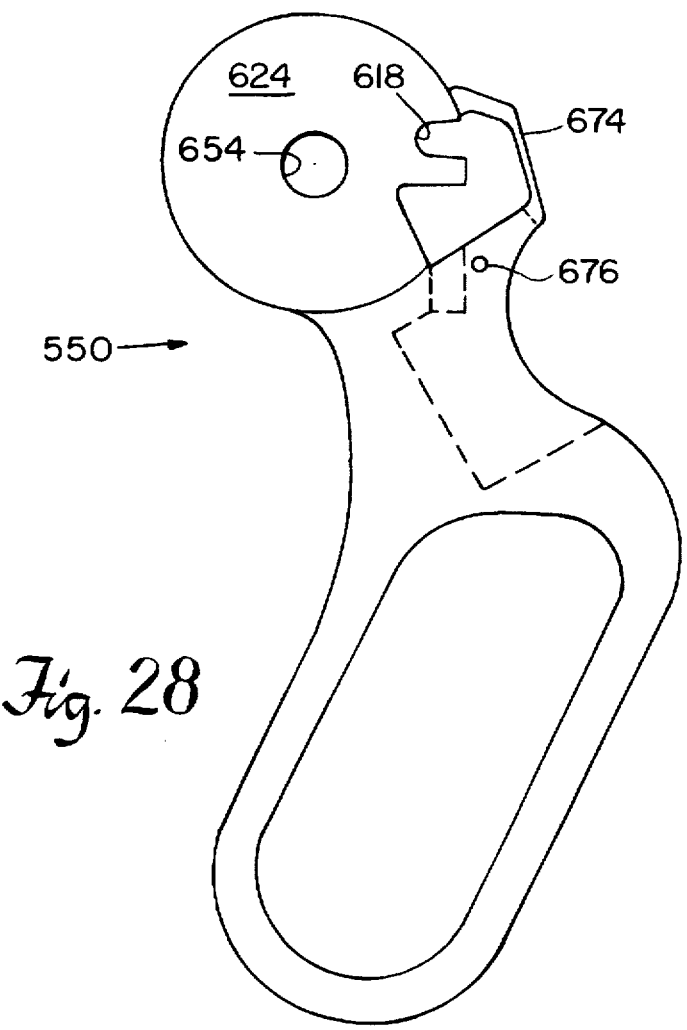
FIG. 28 is a schematic elevational view of the finger loop of the rotatable-port handle assembly.

FIG. 28 is a schematic elevational view of the finger loop 550 of the handle assembly 500 of the present invention. The finger loop 550 comprises finger disk 624 and guard 674. Pivot hole 654 passes through the finger loop 550 approximately at the center of the finger disk 624. The finger disk 624 comprises finger notch 618 engageable by the trigger key 612 to lock the finger disk 624 to the housing disk 627 in either the pistol or the scissor configuration. The finger loop 550 also comprises a pivot hole 676. The pivot 604 passes through this hole 676 to mount the release trigger 602 to the finger loop 550.

FIG. 29 is a schematic elevational view of the thumb loop 552 of the handle assembly 500 of the present invention. The thumb loop 552 comprises a thumb disk 622 having a pivot hole 656 approximately at its center and the thumb notch 616 on its circumference. The thumb notch 616 is engageable by the slide key 610 to lock the thumb disk 622 to the drive cog 504.

FIG. 30a is a schematic elevational view of the drive cog 504 and the torsion spring 555 of the handle assembly 500 of the present invention. FIG. 30b is a side view of the drive cog 504. The drive cog 504 comprises a pivot hole 658 located approximately through its center. The torsion spring 555 rests in a recessed portion 678 of the drive cog 504. The end 666 of the torsion spring is inserted in hole 664. The end 668 of the torsion spring 555 rests in a hole in the top cover 503 (not shown).

Tabs 556 and 558 are formed on the circumference of the drive cog 504. Tab 556 engages a tool assembly to actuate it. Tab 558 engages a tool assembly during installation to ensure proper installation.

The pistol configuration notch 614 and the scissor configuration notch 632 are also formed on the circumference of the drive cog 504. These notches are engageable by the slide key 610 to lock the thumb disk 622 to the drive cog 504 in either the pistol configuration or the scissor configuration.

FIGS. 31a and 31b are schematic elevational views of the release trigger 602 of the handle assembly 500 of the present invention rotated 90° from each other. The release trigger 602 comprises a pivot hole 678 through which pivot 604 passes to mount the release trigger 602 to the finger loop 550. The release trigger 602 also comprises a depression end 606 and a key end 608. The trigger key 612 is located at the key end 608 of the release trigger 602. The release trigger 602 also comprises a slide rail 646. The slide rail 646 mates with the slide groove 648 on the slide member 600. When the drive cog 504 and thumb loop 552 rotate with respect to the housing disk 627 and the finger loop 550, the slide member 600 slides along the release trigger 602, guided by the slide rail 646 and slide groove 648.

FIG. 32 is a schematic elevational view of the slide member 600 of the handle assembly 500 of the present invention. The slide member 600 comprises the slide groove 648 which mates with the slide rail 646 of the release trigger 602. The pivot 604 passes through slot 650 in the slide member 600 to control the extent of travel of the slide member 600. The slide key 610 of the slide member 600 comprises a step 680 (see FIGS. 33a and 33b also). The step 680 is used in controlling the sequencing and depth of engagement of the keys 610 and 612 with the grooves in the disks and drive cog 504. This will be described below in detail.

Figure 33A:
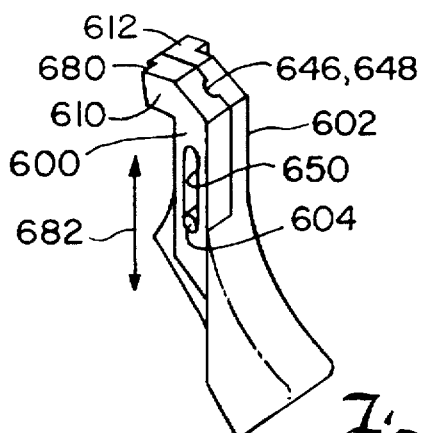
FIG. 33a schematic perspective view of the trigger and slide member of the rotatable-port handle assembly with the slide member at the top of the trigger.
Figure 33B:
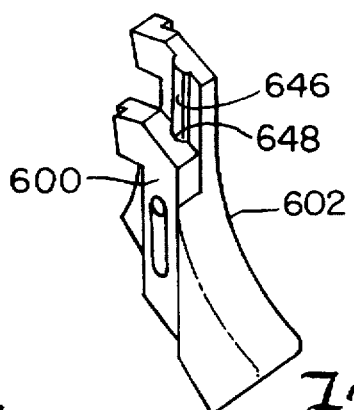
FIG. 33b is a schematic perspective view of the trigger and slide member of-the rotatable-port handle assembly with the slide member at the bottom of the trigger.

FIGS. 33a and 33b are schematic perspective views of the release trigger 602 and slide member 600 of the handle assembly 500 of the present invention. The figures represent the sliding action of the slide member 600 with respect to the release trigger 602.

The slide member 600 slides back and forth along the release trigger 602 as indicated by the arrow 682. FIG. 33a shows the slide member 600 at the top of the release trigger 602. The slide key 610 and the trigger key 612 are substantially aligned. As described above in connection with FIG. 24, when the release trigger 602 and slide member 600 are in this position in an assembled surgical instrument having the handle assembly 500, the thumb loop 552 and the finger loop 550 have been rotated toward each other. Consequently, the tab 556 on the drive cog 504 has been translated back within the port 517, and the tool assembly 12 is in the closed position.

FIG. 33b shows the slide member 600 at the bottom of the release trigger 602. In an assembled surgical instrument having the handle assembly 500, when the release trigger and slide member are in this position, the tool assembly is open. As shown in FIGS. 33a and 33b, the slide member 600 is guided by slide rail 646 on the release trigger 602 and slide groove 648 on the slide member 600. The slot 650 in the slide member 600 and the pivot 604 limit the travel distance of the slide member 600.

FIGS. 34a–f and 35a–f illustrate the steps in the process of rotation from the pistol configuration to the scissor configuration. FIGS. 34a–f are schematic elevational views of the housing disk 627, finger disk 624, thumb disk 622, drive cog 504, release trigger 602 and slide member 600 in various stages of the rotation process. Each of FIGS. 35a–f is a schematic cross-sectional view taken along a cut line shown in one of FIGS. 34a–f. Each of FIGS. 34a–f corresponds to one of FIGS. 35a–f. It should be noted that guard 674 is shown in FIGS. 34a–f but has been omitted from FIGS. 35a–f for purposes of clarity.

Figure 34B:
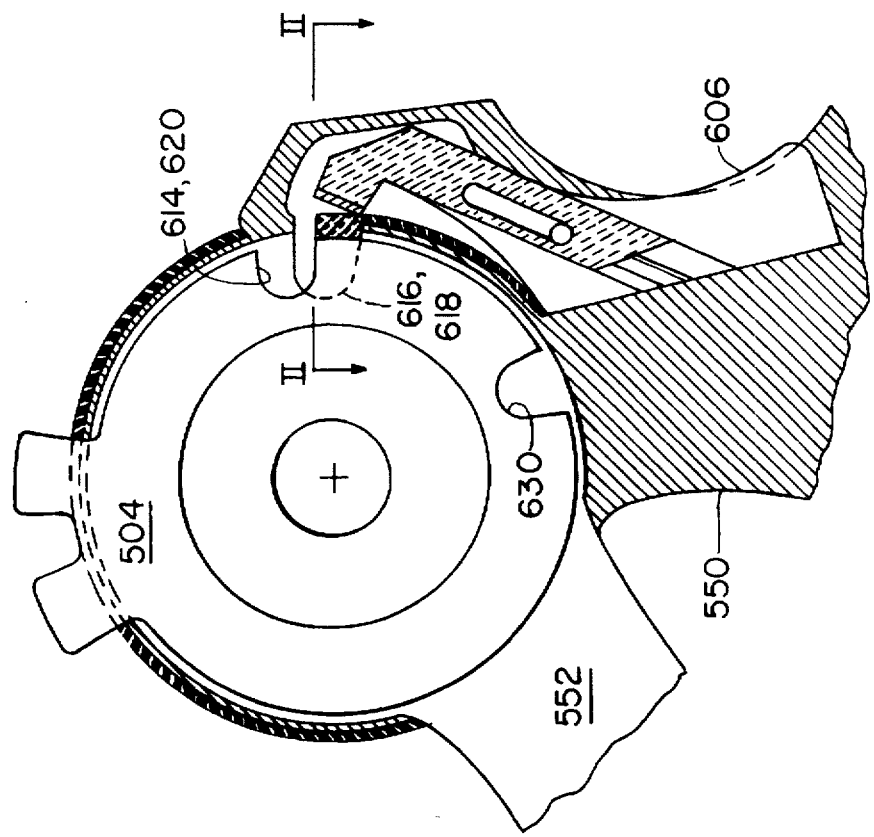
FIGS. 34a–34f are schematic side elevational views of the disks, drive cog, trigger, and slide member of the rotatable-port handle assembly of the present invention, showing various steps in the rotation process.
Figure 34A:
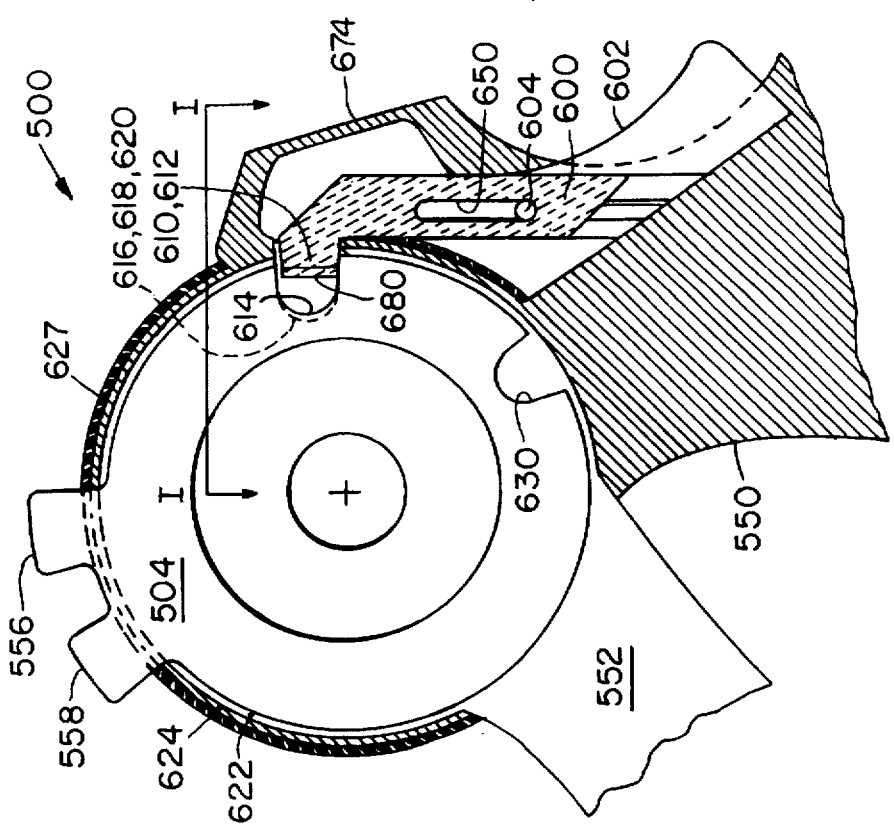

FIGS. 34a and 35a show the handle 500 locked in the pistol configuration before the rotation process begins. The release trigger 602 is in the closed position, and the finger loop 552 and thumb loop 550 are rotated toward each other to the tool-assembly-closed position. As a result, four disk notches, namely, the pistol configuration housing notch 620, the finger notch 618, the thumb notch 616, and the pistol configuration drive cog notch 614 are aligned. Also, the slide member 600 is at the top of the release trigger 602 such that the trigger key 612 and the slide key 610 are aligned.

The trigger key 612 is in engagement with the pistol configuration housing disk notch 620 and the finger disk notch 618. Therefore, the two disks are rotationally fixed to each other. The slide key 610 engages the thumb disk notch 616 and the pistol configuration drive cog notch 614 to rotationally fix the thumb loop 552 to the drive cog 504.

FIGS. 34b and 35b illustrate a first step in the rotation process. The depression region 606 of the trigger 602 has been depressed to rotate the release trigger 602 such that keys 610 and 612 no longer engage notches 614, 616, 618, 620. The finger loop 550 and thumb loop 552 have been rotated slightly in-the clockwise direction relative to the housing disk 627 and the drive cog 504. Therefore, notches 614 and 620 are no longer aligned with notches 616 and 618. It should be noted that the finger loop 550 and the thumb loop 552 may be held together in the tool-assembly-closed position by the user during the rotation process as shown in the figures. This keeps the thumb notch 616 substantially aligned with the finger notch 618 during the process to facilitate locking the handle in the scissor configuration at the end of the rotation process. Also, notches 614 and 620 are drawn as remaining aligned during the process. This need not be the case. There is no coupling between the drive cog 504 and the housing 502 to keep the notch 614 and 620 aligned. However, the tool assembly 12 in the handle port 517 is engaged with tab 556 on the drive cog 504. The frictional forces in the tool assembly will tend-to keep the drive cog 504 stationary with respect to the housing disk 627. In general, the drive cog notches 614 and 630 will move only slightly out of alignment with their corresponding housing disk notches 620 and 632.

As shown more clearly in FIG. 35b, during this step, the trigger key 612 rides on the outer diameter of the housing disk 627 as the finger loop 550 is rotated. Because of the difference in diameters among the other disks and the drive cog 504, the trigger key 612 and slide key 610 do not contact the other disks.

Figure 34D:
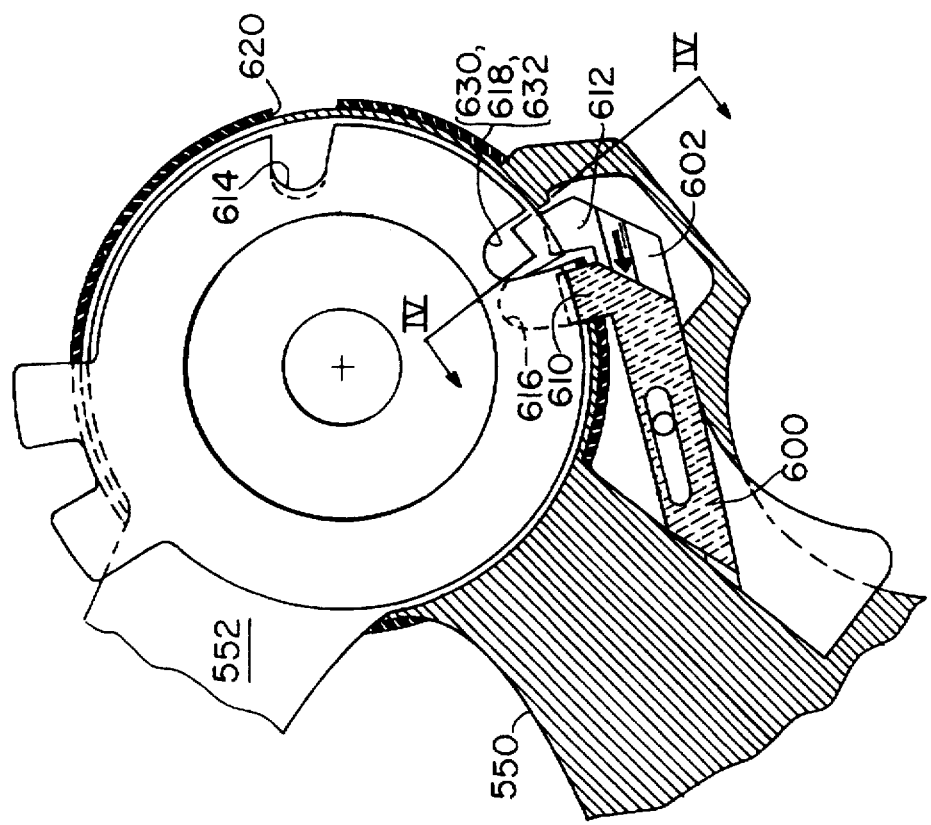
Figure 34C:
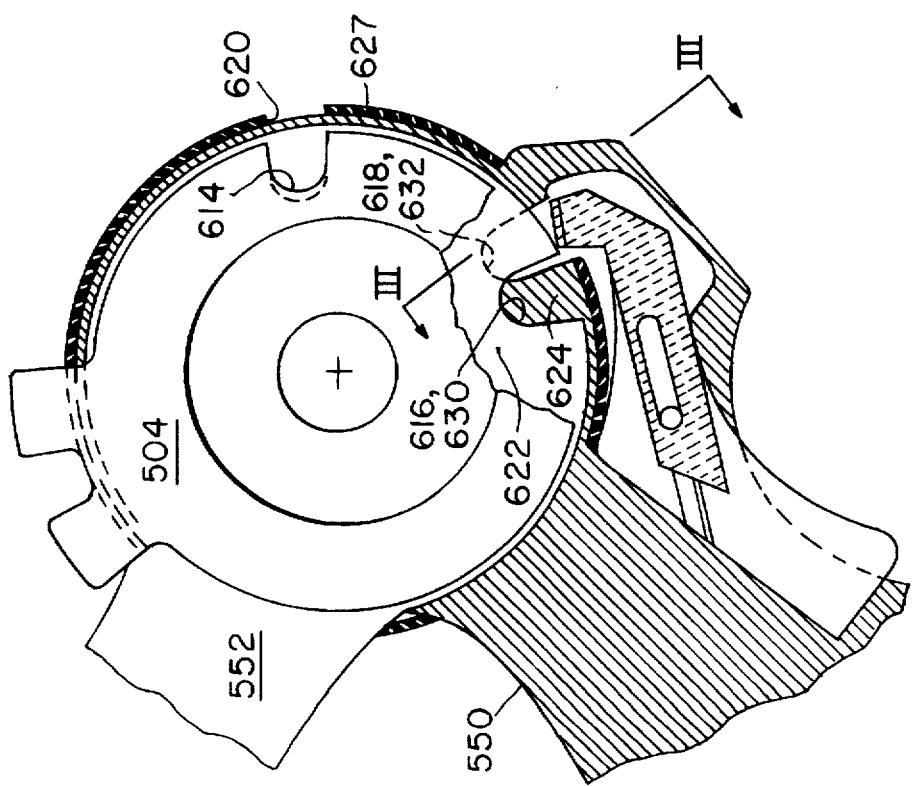

In FIGS. 34c and 35c, the thumb loop 552 and finger loop 550 have been rotated far enough-that the finger loop notch 618 is aligned with the scissor configuration housing disk notch 632. The scissor key 612 is allowed to fall into partial engagement with both notches. However, because the scissor configuration drive cog notch 630 and the thumb disk notch 616 are not aligned with the finger disk notch 618 and the scissor configuration housing disk notch 632, the slide key 610 cannot fall into engagement with the notches 616 and 630. Instead, the key 610 rests on the outer surface of the thumb disk 622.

Referring to FIG. 35c, the trigger key 612 has dropped into partial engagement with the housing disk notch 632 and the finger disk notch 618. This partial engagement is sufficient to lock the finger loop 550 to the housing 502 in the scissor configuration and prevent further rotation. Since the thumb notch 616 and drive cog notch 630 are not also aligned, the slide key 610 rests on the outer surface of the thumb disk 622. Because the slide member 600 is coupled to the release trigger 602 via the slide rail 646 and slide groove 648, the slide key 610 prevents the trigger key 612 from falling completely into engagement with the notches 618 and 632.

In FIGS. 34d and 35d, following rotation of the thumb loop 552, the slide key 610 has fallen into partial engagement with the thumb notch 616. Because the scissor configuration drive cog notch 630 is not aligned with the thumb notch 616, the slide key 610 and thus the trigger key 612 cannot fall totally into engagement with the notches. Step.680 in the slide key 610 rides on the outer surface of the drive cog 504, thus preventing the trigger 602 from rotating into the closed position.

In order for the slide key 610 to engage the thumb notch 616 as shown, the thumb loop 550 was rotated back and forth to align the slide key 610 with the notch 616. At the same time, the slide member 600 slid along the release trigger 602 to facilitate the alignment. FIGS. 34d and 35d show the slide member 600 no longer at the top of the release trigger 602. It has translated an amount required for the slide key 610 to line up with the thumb notch 616. With the slide key 610 now partially engaged in notch 616, the step 680 in the slide key 610 rides on the outer surface of the drive cog 504. The step 680 allows the slide key to fall far enough into the thumb notch 616 such that it will not be able to inadvertently disengage the notch 616 during subsequent alignment of the slide key 610 with the notch 630 on the drive cog 504.

Figure 34F:
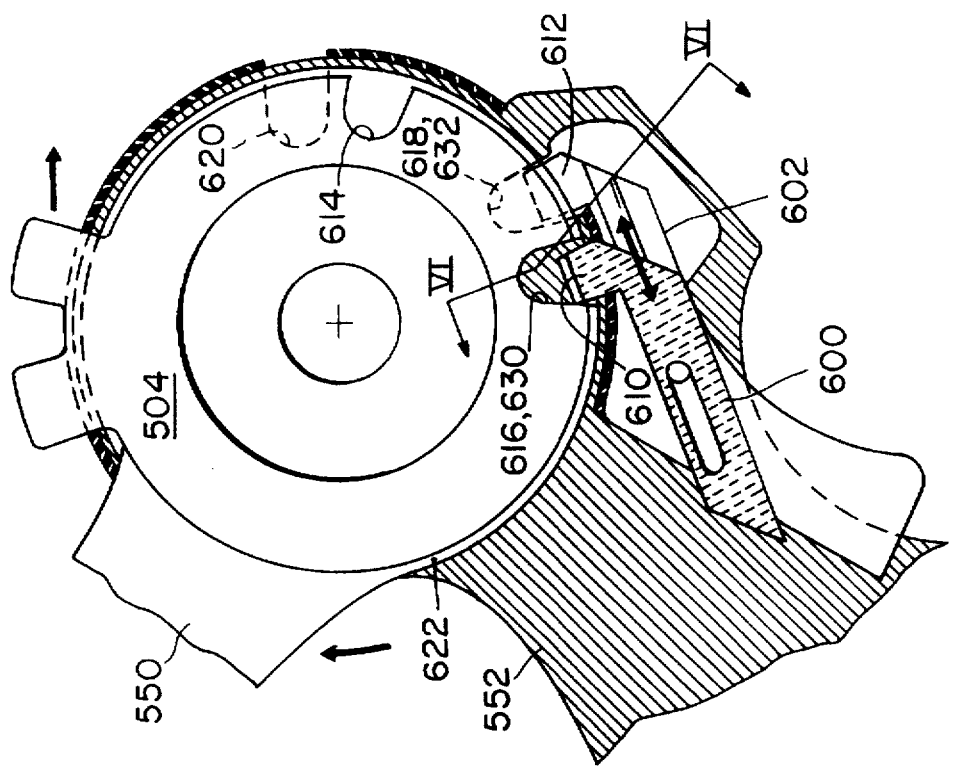
Figure 34E:
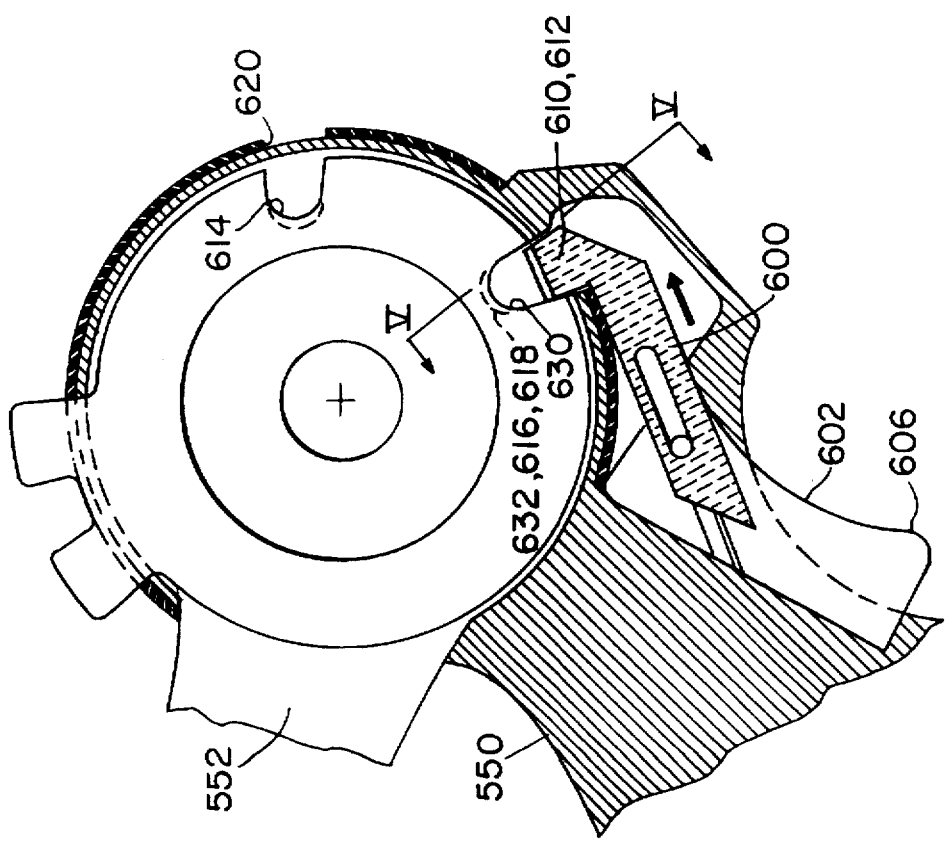

FIGS. 34e and 35e show the final step of the rotation process. The thumb loop 552 has been rotated back and forth until the slide key 610 was dragged into alignment with the scissor configuration notch 630 in the drive cog 504. The slide key 610 has fallen into complete engagement with notches 618 and 630. Since it is no longer inhibited by the slide key 610, the trigger key 612 has dropped into complete engagement with notches 618 and 632. The release trigger 602 has rotated completely into the closed position.

In FIGS. 34e and 35e, all four notches 630, 616, 618, and 632 are in alignment, and the slide-member 600 is at the top of the trigger 602. Thus, the handle 500 is in the tool-assembly-closed position. However, this need not be the case. The rotation process need not conclude in this position.

FIGS. 34f and 35f illustrate the tool actuation function in the scissor configuration. The thumb loop 550 is rotated with respect to the finger loop 552. Because the slide key 610 couples the thumb disk 622 to the drive cog 504, the drive cog 504 also rotates. The slide member 600 slides along the release trigger 602. During tool actuation, the trigger key 612 remains stationary within the finger notch 618 and the scissor configuration housing notch 630. Therefore, the scissor configuration is maintained.

While this invention has been particularly shown and described with references to preferred embodiments thereof, it will be understood by those skilled in the art that various changes in form and details may be made therein without departing from the spirit and scope of the invention as defined by the appended claims.

We claim:

1. A surgical instrument comprising:
  a tool assembly comprising:
    a sleeve;
    jaws pivotable relative to each other, each jaw having an open-ended slot open at a proximal end of the jaw, said jaws being pivotably mounted to a distal end of the sleeve;
    an extension within the sleeve longitudinally translatable relative to the sleeve in and out of the open-ended slots at the proximal ends of the jaws, said extension being engageable with inner walls of the open-ended slots to drive the jaws toward open and closed positions when said extension is in the open-ended slots; and
  a handle assembly for retaining the tool assembly and longitudinally translating the extension relative to the sleeve.

2. The surgical instrument of claim 1 wherein the tool assembly and handle assembly are detachable.

3. The surgical instrument of claim 1 wherein the extension is translatable out of the open-ended slots such that the jaws are detachable from the sleeve and replaceable on the sleeve.

4. The surgical instrument of claim 1 wherein the tool assembly further comprises a compressible pivot for removably mounting the jaws to the distal end of the sleeve.

5. The surgical instrument of claim 1 wherein
  the distal end of the sleeve comprises an elastic material such that the distal end of the sleeve is spreadable to allow the jaws to be removed from the sleeve and replaced on the sleeve.

6. The surgical instrument of claim 1 wherein the tool assembly further comprises a cleaning port for allowing a cleaning fluid to be introduced into the tool assembly, the extension being translatable out of the open-ended slots in the jaws to open the cleaning port.

7. The surgical instrument of claim 1 further comprising:
  a pivot pin coupled to the distal end of the sleeve for mounting the jaws; and
  a drive pin coupled to the extension, said drive pin being engageable with the inner walls of the slots in the jaws to pivot the jaws.

8. The surgical instrument of claim 1 wherein the tool assembly comprises a rotator for rotating the tool assembly about a longitudinal axis of the tool assembly to a desired position.

9. The surgical instrument of claim 1 further comprising means for providing an electrical connection to the sleeve.

10. A surgical instrument comprising:
  a tool assembly comprising:
    a sleeve having a distal end to which jaws can be mounted, said distal end comprising an elastic material such that the distal end can be spread to allow the jaws to be inserted into the distal end and removed from the distal end;
    jaws pivotable relative to each other, each jaw having an open-ended slot open at a proximal end of the jaw, said jaws being pivotably mounted to the distal end of the sleeve;
    an extension within the sleeve longitudinally translatable relative to the sleeve in and out of the open-ended slots at the proximal ends of the jaws, said extension being engageable with inner walls of the open-ended slots to drive the jaws toward open and closed positions when said extension is in the open-ended slots; and a handle assembly for retaining the tool assembly and longitudinally translating the extension relative to the sleeve.

11. A surgical tool assembly comprising:

a sleeve;

jaws pivotable relative to each other, each jaw having an open-ended slot at a proximal end of the jaw, the jaws being pivotably mounted by a pivot to a distal end of the sleeve; and an extension within the sleeve longitudinally translatable relative to the sleeve in and out of the open-ended slots at the proximal ends of the jaws, said extension being engageable with inner walls of the open-ended slots to drive the jaws toward open and closed positions when said extension is in the open-ended slots.

12. The tool assembly of claim 11 wherein the pivot is compressible such that the jaws are removable from the sleeve.

13. The tool assembly of claim 11 further comprising a cleaning port for allowing a cleaning fluid to be introduced into the tool assembly, the extension being translatable out of the open-ended slots in the jaws to open the cleaning port.

14. The tool assembly of claim 11 wherein the distal end of the sleeve comprises an elastic material such that the distal end of the sleeve is spreadable to allow the jaws to be removed from the sleeve and replaced on the sleeve.

15. The tool assembly of claim 11 further comprising:

a pivot pin coupled to the distal end of the sleeve for mounting the jaws; and a drive pin coupled to the extension, said drive pin being engageable with the inner walls of the slots in the jaws to pivot the jaws.

16. A surgical tool assembly comprising:

a sleeve having a distal end to which jaws can be mounted, said distal end comprising an elastic material such that the distal end can be spread to allow the jaws to be inserted into the distal end and removed from the distal end;

jaws pivotable relative to each other, each jaw having an open-ended slot open at a proximal end of the jaw, the jaws being pivotably mounted to the distal end of the sleeve such that the jaws are removable from the sleeve and replaceable on the sleeve; and an extension within the sleeve longitudinally translatable relative to the sleeve in and out of the open-ended slots at the proximal ends of the jaws, said extension being engageable with inner walls of the open-ended slots to drive the jaws toward open and closed positions when said extension is in the open-ended slots.

17. The surgical tool assembly of claim 16 wherein the extension is translatable out of engagement with the jaws to allow the jaws to be removed from the sleeve and replaced on the sleeve.

18. A surgical jaw assembly comprising:

first and second jaws, each jaw having a proximal end and a distal end;

a pivot pivotably attaching the jaws; and an open-ended slot open at the proximal end of each jaw, inner walls of said slots being engageable by a driving member to open and close the distal ends of the jaws as the driving member translates back and forth within the slots.

19. The surgical jaw assembly of claim 18 wherein the pivot comprises:

first and second pivot ends; and a spring disposed between the pivot ends and biasing the pivot ends away from each other such that the pivot is compressible by forcing the first and second pivot ends toward each other.

20. A surgical instrument comprising:

an elongate sleeve;

an elongate extension within the sleeve longitudinally translatable relative to the sleeve; and at least one pivotable jaw having an open-ended slot open at a proximal end of the at least one pivotable jaw, said at least one pivotable jaw coupled to a distal end of the sleeve such that relative longitudinal translation between the extension and the sleeve causes the at least one pivotable jaw to pivot when the extension engages the open-ended slot of the at least one pivotable jaw;

wherein the distal end of the sleeve comprises an elastic material such that the distal end of the sleeve is spreadable to uncouple the at least one pivotable jaw from the sleeve.

21. A surgical tool assembly comprising:

at least one pivotable jaw having an open-ended slot open at a proximal end of the at least one pivotable jaw, said at least one pivotable jaw coupled to the tool assembly; and an extension within the tool assembly longitudinally translatable relative to the at least one pivotable jaw, said extension being engageable with the inner wall of the open-ended slot to drive the at least one pivotable jaw toward open and closed positions when said extension is in the open-ended slot.

* * * * *